US006344203B1

(12) United States Patent
Sandrin et al.

(10) Patent No.: US 6,344,203 B1
(45) Date of Patent: *Feb. 5, 2002

(54) MIMICKING PEPTIDES IN CANCER THERAPY

(75) Inventors: Mauro Sergio Sandrin; Ian Farquar Campbell McKenzie, both of Brunswick; Vasso Apostolopoulos, St. Albans, all of (AU)

(73) Assignee: The Austin Research Institute (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/043,731
(22) PCT Filed: Sep. 27, 1996
(86) PCT No.: PCT/AU96/00617
§ 371 Date: Jun. 23, 1998
§ 102(e) Date: Jun. 23, 1998
(87) PCT Pub. No.: WO97/11715
PCT Pub. Date: Apr. 3, 1997

(30) Foreign Application Priority Data

Sep. 27, 1995 (AU) .............................................. PN5680

(51) Int. Cl.[7] .............................................. A61K 39/00
(52) U.S. Cl. ................... 424/277.1; 514/12; 424/184.1; 424/185.1
(58) Field of Search ......................... 514/12; 530/324; 424/184.1, 185.1, 277.1

(56) References Cited

U.S. PATENT DOCUMENTS 5,744,144 A * 4/1998 Finn et al. ................. 424/177.1
5,827,666 A * 10/1998 Finn et al. .................... 435/7.1

FOREIGN PATENT DOCUMENTS

WO      WO 95/18415      7/1995     ........... C07K/14/47

OTHER PUBLICATIONS

Villarroya et al, Eur. J. Biochem. vol. 180 p. 191, 1989.*
CA 122:47806, 1994.*
Ezzell, J. NIH Research vol. 7 p. 46, Jan. 1995.*
Wucherpfennig, K.W., et al. (1995) "Molecular Mimicry in T Cell Mediated Autoimmunity: Viral Peptides Activate Human T Cell Clones Specific for Myelin Basic Protein" Cell 80:695–705.
Davies, J.M., (1997) "Molecular Mimicry: Can Epitope Mimicry Induce Autoimmune Disease?" Immunol Cell Biol 75:113–126.
Durinovic–Bello, I, (1998) "Autoimmune Diabetes: The Role of T Cells, MHC Molecules and Autoantigens". Autoimmunity 27:159–177.

Murali. R., et al., (1997) "Molecular Recognition of a Peptide Mimic of the Lewis Y Antigen by an Anti–Lewis Y Antibody". J Mol Recognit 10:269–276.
Apostolopoulos, V., et al., (1998) "Peptide Mimics of a Tumor Antigen Induce Functional Cytotoxic T Cells" Nat Biotechnol 16:276–280.
Apostolopoulos, V., et al. (1996) "Cell–Mediated Immune Responses to MUC1 Fusion Protein Coupled to Mannan". Vaccine 14:930–938.
Apostolopoulos, V., et al. (1995) "Oxidative/Reductive Conjugation of Mannan to Antigen Selects for T1 or T2 Immune Responses". Proc Natl Acad Sci USA 92:10128–10132.
Karanikas, V., et al. (1997) "Antibody and T Cell Responses of Patients with Adenocarcinoma Immunized with Mannan–MUC1 Fusion Protein". J Clinical Invest 100:2783–2792.
Apostolopoulos, V., et al., (1998) "MUC1 Cross Reactive Galα(1,3)Gal Abs in Humans Switch Immune Responses from Cellular to Humoral", Nature Med 4:315–320.
Vaughn, H.A., et al., (1994) "Galα(1, 3) Gal is the Major Xenoepitope Expressed on Pig Endothelial Cells Recognized by Naturally Occuring Cytotoxic Antibodies". Transplanation 58:879–884.
Sandrin, M.S., et al., (1995) "Anti–pig IgM Antibodies in Human Serum Predominantly React with Galα(1,3)Gal Epitopes", Proc Natl Acad Sci USA 90:11391–11395.
Vaughan, H.A., et al., (1996) "Recognition of an Octapeptide Sequence by Multiple Galα(1,3)Gal–binding Proteins". Xenotransplantation 3:18–23.
Sandrin, M.S., et al., (1997) "Natural Human Anti–Galα(1, 3)Gal Antibodies React With Human Mucin Paptides". Glycoconj J 14:97–105.
Oldenburg, K.R., et al., (1992) "Peptide Ligands for a Sugar–Binding Protein Isolated From a Random Peptide Library". Proc. Natl. Acad. Sci. USA 89, 5393–5397.
Scott, J.K., et al., (1992) "A Family of Concanavilin A–binding Peptides From a Hexapeptide Epitope Library". Proc. Natl. Acad. Sci. USA 89, 5398–5402.
Hoess, R., et al., (1993) "Identification of a Peptide Which Binds to the Cabrohdrate–Specific Monoclonal Antibody B3". Gene 128, 43–49.
Kieber–Emmons, T., et al., (1997) "Peptide Mimicry of Adenocarcinoma–Associated Carbohydrate Antigens". Hybridoma 16, 3–10.
Agadjanyan, M., et al., (1997) "Peptide Mimcry of Carbohydrate Epitopes on Human Immunodeficiency Virus". Nature Biotechnol. 15, 547–551.

(List continued on next page.)

*Primary Examiner*—Sheela Huff
(74) *Attorney, Agent, or Firm*—Medlen & Carroll, LLP

(57) ABSTRACT

Peptide mimicks of MUC1 or other cancer peptides which can be included in cancer vaccines and used in therapeutic methods for the treatment of cancer patients.

13 Claims, 17 Drawing Sheets

OTHER PUBLICATIONS

Figure 2A:
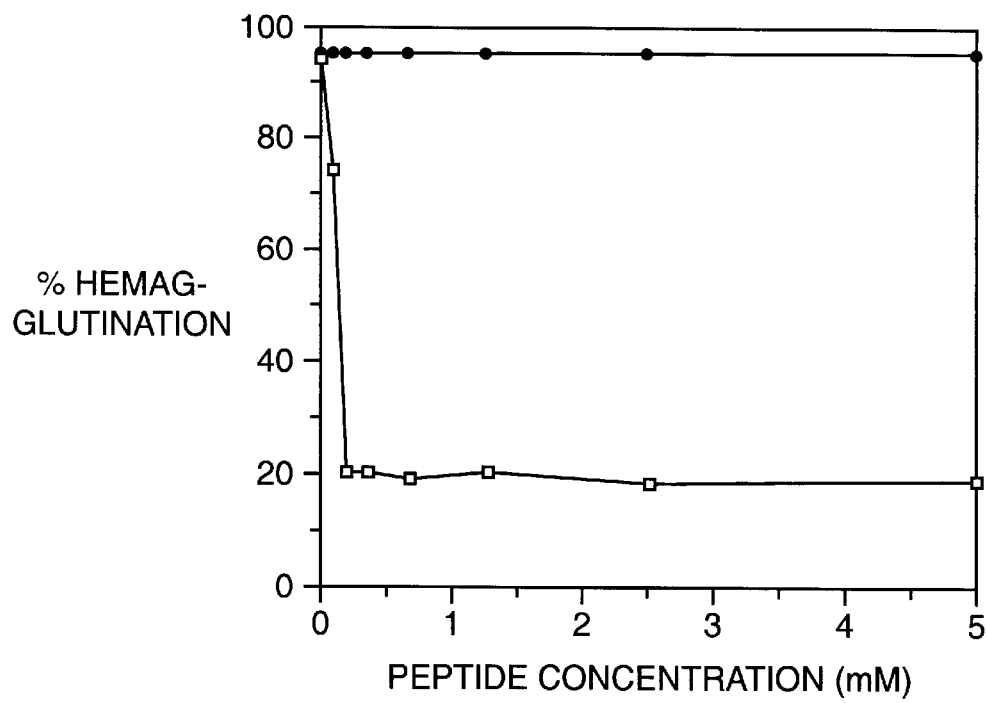

Harris, S.L., et al., (1997) "Exploring the Basis of Peptide–Carbohydrate Cross Reactivity: Evidence for Discrimination by Peptides Between Closely Related AntiCarbohydrate Antibodies". Proc. Natl. Acad. Sci. USA 94, 2454–2459.

Pincus, S. H., et al., (1998) "Peptides That Mimic the Group B Streptococcal Type III Capsular Polysaccharide Antigen". J. Immunol. 160, 293–298.

Valadon, P., et al., (1996) "Peptide Libraries Define the Fine Specificity of Anti–Polysaccharide Antibodies to *Cryptococcus Neoformans*". J. Mol. Biol. 261, 11–22.

Phalipon, A., et al., (1997) "Induction of Anti–Carbohydrate Antibodies by Phage Library–selected Peptide Mimics". Eur. J. Immunol. 27, 2620–2625.

Taki, T., et al., (1997) "Preparation of Peptides Which Mimic Glycosphingolipids by Using Phage Peptide Library and Their Modulation on β–Galactosidase Activity". FEBS Lett. 418, 219–223.

Saleh, M. N., et al., (1993) "Generation of a Human Anti–Idiotypic Antibody that Mimics the GD2 Antigen". J. Immunol. 151, 3390–3398.

Westerink, M. A., et al., (1993) "Anti–Idiotypic Antibodies as Vaccines Against Carbohydrate Antigens". Springer Semin. Immunopathol. 15, 227–234.

Westerink, M. A. J., et al., (1995) "Peptide Mimicry of the Meningococcal Group C Capsular Polysaccharide". Proc. Natl. Acad. Sci. USA 92,4021–4025.

Shikhman, A. R., et al., (1993) "A Subset of Mouse Monoclonal Antibodies Cross–reactive with Cytoskeletall Proteins and Group A Streptococcal M Proteins Recognizes N–acetyl–β–D–glucosamine". J. Immunol. 151, 3902–3913.

Shikhman, A. R., et al., (1994) "Cytokeratin Peptide SFGS-GFGGY Minics N–acetyl–β–D–glucosamie in Reaction with Antibodies and Lectins, and Induces in Vivo Anti–Carbohydrate Antibody Response". J. Immunol. 153, 5593–5606.

Xing, P–X., et al., (1989) "Monoclonal Antibodies Reactive with Mucin Expressed in Breast Cancer". Immunol Cell Biol 67:183–95.

Lofthouse, S.A., et al., (1997) "Induction of $T_1$ (CTL) and/or $T_2$ (Antibody) Response to a Mucin–1 Tumor Antigen", Vaccine 15:1586–1593.

Apostolopoulos, V., et al., (1997) "MUC1 Peptide Epitopes Associated With Five Different H2 Class I Molecules", Eur J Immunol 27:2579–2587.

Apostolopoulos, V., et al., (1997) "Induction of HLA–A2 Restricted Cytotoxic T Lymphocytes to the MUC1 Human Breast Cancer Antigen", J Immunol 159:5211–5218.

Mosmann, T. R., et al., (1986) "Two Types of Murine Helper T Cell Clone. I. Definition According to Profiles of Lymphokine Activities and Secreted Proteins", J Immunol 136:2348–2357.

Coffman, R.L., et al., (1991) "Role of Cytokines in the Differentiation of CD4+ T–cell Subsets in Vivo", Immunol Rev 123:189–207.

Salgame, P., et al., (1991) "Differing Lymphokine Profiles of Functional Subsets of Human CD4 and CD8 T Cell Clones", Science 254:279–282.

Kelso, A. et al., (1998) "Coexpression of Granulocyte–Macrophage Colony Stimulating Factor, Gamma Interferon, and Interleukins 3 and 4 is Random in Murine Alloreactive T–Lymphocyte Clones", Proc Natl Acad Sci USA 85:9189–9193.

Paliard, X., (1988) "Simultaneous Production of IL–2, IL–4, and IFN–gamma by Activated Human CD4+ and CD8+ T Cell Clones", J Immunol 14:849–855.

Parish, C.R., (1971) "Immune Response to Chemically Modified Flagellin. II. Evidence for a Fundamental Relationship Between Humoral and Cell–Mediated Immunity", J Exp Med 13:21–47.

Urban, J.F., Jr, et al., (1992) "The Importance of Th2 Cytokines in Protective Immunity to Nematodes", Immunol Rev 127:205–220.

Hsieh, C.S., et al., (1993) "Development of TH1 CD4+ T Cells Through IL–12 Produced by Listeria–Induced Macrophages", Science 260:547–549.

Parish, C.R., (1972), "The Relationship Between Humoral and Cell–Mediated Immunity", Transplant Rev 13:35–66.

Mitchison, N.A., (1964), "Induction of Immunological Paralysis in Two Zones of Dosages", Proc R Soc Lond 161:275–292.

Pietersz, G.A., et al., (1998), "Parameters for Using Mannan–MUC1 Fusion Protein to Induce Cellular Immunity", Cancer Immunol Immunother 45:321–326.

Apostolopoulos, V., et al., (1995), "Oxidative/Reductive Conjugation of Mannan to Antigen Selects for $T_1$ or $T_2$ Immune Responses", Proc Natl Acad Sci USA 92:10128–10132.

Galili, U., et al., (1988), "Man, Apes, and Old World Monkeys Differ From Other Mammals in the Expression of Alpha–Galactosyl Epitopes on Nucleated Cells", J Biol Chem 263:17755–17762.

Joziasse, D.H., et al, (1991), "Characterization of an Alpha 1–3–Galactosyltransferase Homologue on Human Chromosome 12 That is Organized as a Processed Pseudogene", J Biol Chem 266:6991–6998.

Larsen, R.D., et al., "Frameshift and Nonsense Mutations in a Human Genomic Sequence Homologous to a Murine UDP–Gal:beta–D–Gal (1,4)–D–GlcNAc alpha(1,3)–Galactosyltransferase cDNA", (1990) J Biol Chem 265:7055–7061.

Galili, U., et al., (1997) "Natural Anti–Gal Antibody as a Universal Augmentor of Autologous Tumor Vaccine Immunogenicity", Immunol Today 18:281–285.

Henion, T.R., et al., (1997) "Synthesis of alpha–gel Epitopes on Influenza Virus Vaccines, by Recombinant alpha 1,3 Galactosyltransferase, Enables the Formation of Immune Complexes with the Natural Anti–Gal Antibody", Vaccine 15:1174–1182.

Celis, E., et al., (1987) "Modulation of the Immunological Response to Hepatitis B Virus by Antibodies", Hepatology 7:563–568.

Bouige, P., et al., (1996) "Molecular Analysis of the Modulatory Factors of the Response to HBsAg in Mice as an Approach to HBV Vaccine Enhancement", Immunol Med Microbiol 13:71–79.

Galili, U., et al., (1996) "Enchancement of Antigen Presentation of Influenza Virus Hemagglutinin by the Natural Human Anti–Gal Antibody", Vaccine 14 : 321–328.

Apostolopoulos, V., et al., (1998) "Anti–MUC1 Antibodies React Directly with MUC1 Peptides Presented by Class I H2 and HLA Molecules", J Immunol 161:767–775.

Apostolopoulos, V., et al., (1993), "Production of Anti–Breast Cancer Monoclonal Antibodies Using a Glutathione–S–transferase–MUC1 Bacterial Fusion Protein", Br. J. Cancer 67:713–720.

Arklie, J., et al., (1981), "Deferentiation Antigens Expressed by Epithelial Cells in the Lactating Breast are also Detectable in Breast Cancers", Int. J. Cancer, 28:23–29.

Burcell J., et al., (1987), "Development and Characterization of Breast Cancer Reactive Monoclonal Antibodies Directed to the Core Protein of the Human Milk Mucin", Cancer Res. 47:5476–7482.

Gendler J.D., et al., (1995), "Epithelial Mucin Genes", Annu Rev Physiol 265:607–634.

Hayes C.E., et al., (1974), "An α–D–Galactosyl–binding Lectin from *Bandeiraea Simplicifolia* Seeds", J Biol Chem 249:1904–1914.

Jerome K.R., et al., (1992), "Expression of Tumor–associated Epitopes on Epstein–Barr Virus Immortalized B–Cells and Burkitt's Lymphomas Transfected with Epithelial Mucin Complementary DNA[1]", Cancer Res 52:5985–5990.

McKenzie I.F.C., et al., "Distribution of the Major Xenoantigen (Galα(1,3)Gal) for Pig to Human Xenografts". Transplant Immunol (1994); 2:81.

Merrifield R.B., (1963), "Solid Phase Peptide Synthesis. I. The Synthesis of a Tetrapetide", J Am Chem Soc 85:2149–2154.

Merrifield R.B. (1965) "Automated Synthesis of Peptides". Science 1965; 150:178.

Sandrin M.S., et al., (1992), "Isolation and Characterization of cDNA Clones for Mouse Ly–9[1]", J Immunol 149:1636–1641.

Sandrin M.S., et al., (1994), "Identification of Gal(α1,3)Gal as the Major Epitope for Pig–to–Human Vascularised Xenografts", Transplant Revs 8:134–149.

Sandrin M.S., et al., (1994), "Characterization of cDNA Clones for Porcine α(1,3) Galactosyl Transferase: The Enzyme Generating the Galα(1,3) Gal Epitope", Xenotransplanation 1:81–88.

Sandrin M.S., et al., (1994), Galα(1,3)Gal, the Major Xenoantigen(s) Recognised in Pigs by Human Natural Antibodies, Immunol Revs 141:169–190.

Stacker S.A., et al, (1995), "A New Breast Carcinoma Antigen Defined by a Monoclonal Antibody", J. Natl. Cancer Inst. 75:801–811.

Vaughan H.A., et al., "The Isolation of cDNA Clones for CD–48". Immunogenetics (1991); 33:113.

Vaughan H.A., et al., "Biochemical Studies of Pig Xenoantigens Detected by Naturally Occurring Antibodies and the Galactose α1–3Galactose Reactive Lectin". Transplanation (1995); 59:102.

Xing P–X., et al., (1992), "Epitope Mapping of Anti–Breast and and Anti–Ovarian Mucin Monoclonal Antibodies", Mol Immunol 29:641–650.

Xing P–X., et al., (1989), "Monoclonal Antibodies Reactive with Mucin Expressed in Breast Cancer", Immunol. Cell. Biol. 67:813–185.

E. Blume et al., "Time of Truth for Cancer Vaccines", J. Nat. Cancer Inst. 86, 330 (1994).

J.Taylor–Papadimitriou, et al., "Exploiting Altered Glycosylation Patterns in Cancer: Progress and Challenges in Diagnosis and Therapy", TIBTECH 12, 227 (1994).

Xing, P–X., et al., "Second Generation Anti–MUC1 Peptide Monoclonal Antibodies", Cancer Res. 52, 2310 (1992).

D.L. Barnd, et al., "Specific, Major Histocompatibility Complex–Unrestricted Recognition of Tumor–Associated Mucins by Human cytotoxic T Cells", Proc. Natl. Acad. Sci. U.S.A. 86, 7159 (1989).

K.R. Jerome et al., "Tumor–Specific Cytotoxic T Cell Clones From Patients with Breast and Pancreatic Adenocarcinoma Recognize EBV–I Immortalized B Cells Transfected with Polymorphic Epithelial Mucin Complementary DNA[1]", J. Immunol. 151, 1654 (1993).

G.C. Ioannides et al., "Cytotoxic T Cells from Ovarian Malignant Tumors Can Recognize Polymorphic Epithelial Mucin Core Peptides", J. Immunol. 151, 3693 (1993).

Apsotolopoulous, V., et al., "Cell–Madiated Immune Responses to MUC1 Fusion Protein Coupled to Mannan", Vaccine, 14, 930 (1996).

Apostolopoulos, V., et al., "Oxidative/Reductive Conjugation of of Mannan to Antigen Selects for $T_1$ or $T_2$ Immune Responses", Proc. Natl. Acad. Sci. U.S.A. 92, 10128 (1995).

Lefkovits, I., et al., "Limiting Dilution Analysis of the Cells of Immune System. I. The Clonal Basis of the Immune Response", Immunology Today 5, 265 (1984).

Taswell, C., "Limiting Dilution Assays for the Determination of Immunocompetent Cell Frequencies", J. Immunol. 126, 1614 (1981).

Fazekas, S., et al., "The Evaluation of Limiting Dilution Assays", J. Immunol. Methods 49, R11 (1982).

Arklie, J. et al., Differentiation Antigens Expressed by Epithelial Cells in the Lactating Brest Are Also Detectable in Breast Cancers, Int. J. Cancer: vol. 28, pp. 23–29 (1981).

Gender, S, et al., Epithelian Mucin Genes, Annu. Rev. Physiol. vol. 57, pp. 607–634 (1995).

* cited by examiner

DGHWANWV
DGNWAIYV
DADWAGFI
DAHWESWL
DGHWDSWL
VSTFDSWL
GTSFDDWL

FIG. 1

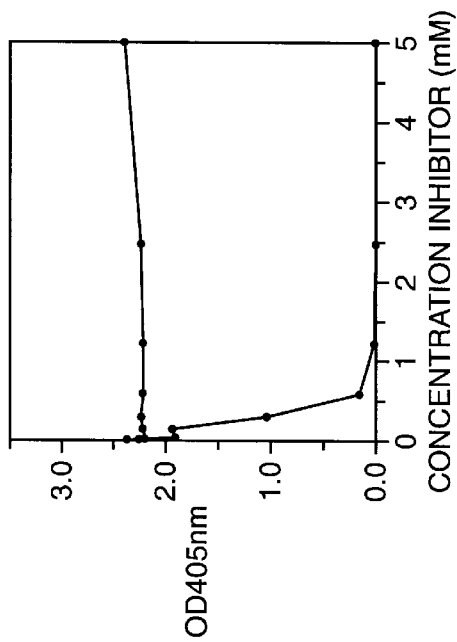
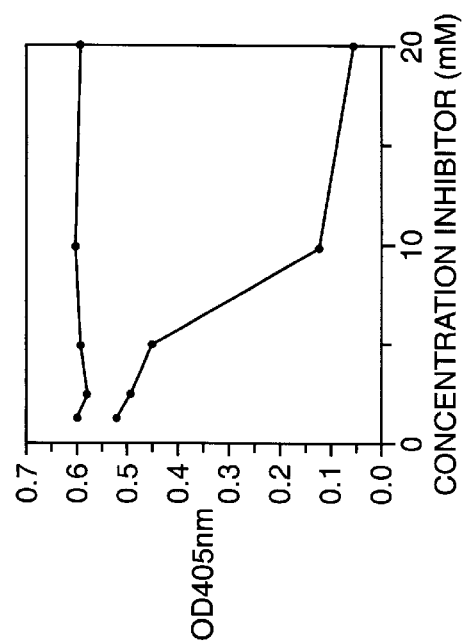
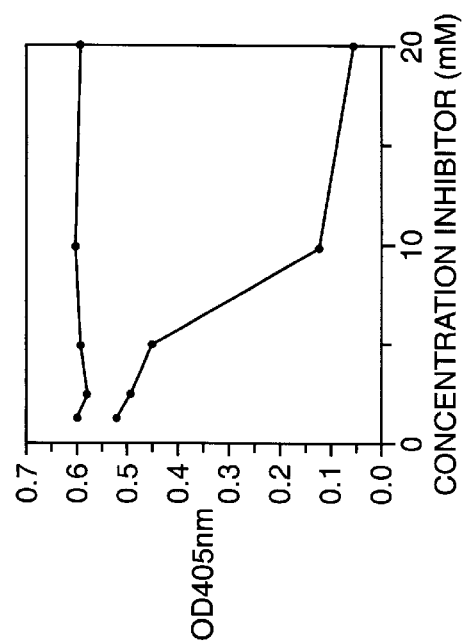
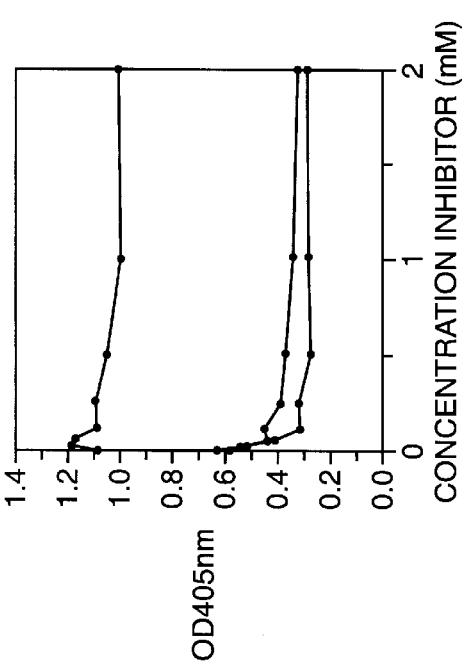
FIG. 5A
FIG. 5B
FIG. 5C
FIG. 5D

MIMICKING PEPTIDES IN CANCER THERAPY

FIELD OF THE INVENTION

The present invention relates to anti-Galα(1,3)Gal antibody binding peptides and to the use of such peptides in cancer therapy.

BACKGROUND OF THE INVENTION

A successful vaccine for cancer immunotherapy requires the identification of a suitable target antigen and the production of a cytotoxic T cell response (25). Cancer mucins, particularly MUC1 (2), provide a suitable target in cancer as there is a 10-fold increase in mucin expression, a ubiquitous (rather than polar) distribution on the cell surface, and altered glycosylation which reveals normally hidden peptide sequences (particularly an anti-MUC1 antibody detected epitope: the amino acids APDTR from the variable number of tandem repeat region (VNTR) (27). These changes apparently absent in normal mucin generate new targets for immunotherapy (28). The APDTR sequence is immunogenic in mice leading to antibody formation whether the antigen is administered as purified mucin (MHFG) or peptides (29). Such studies of immunogenicity in mice would be of little relevance to humans, were it not for the findings that tumour specific CTLp exist in the lymph nodes of patients with cancers of either breast, ovary or pancreas (30). Thus, theoretically, patients could be immunised with MUC1 peptide sequences to convert their CTLp into functional CTLs which should have a therapeutic anti-cancer effect.

The applicants have previously shown in a murine MUC1+ tumour model, that a 20 mer MUC1 VNTR peptide sequence (made as a GST fusion protein (FP)) when coupled to oxidised mannan (M-FP-oxidised) generates H-2 restricted CTLs which protects from challenge with MUC1+ mouse tumours, and in addition leads to the rapid reversal of the growth of established MUC1+ tumours (stimulation of $T_1$ T cells) (International Patent Application No. PCT/AU9400789) (31,32). Based on the foregoing, adenocarcinoma patients have been immunised with M-FP and antibody and cellular responses generated. Nonetheless it is of interest that patients could be immunised, albeit weakly, against a self peptide, and both T and B cell tolerance appears to be broken. Despite the immune responses noted, MUC1 is a self peptide occurring in normal mucin in tissues such as breast, kidney, lung, ovary. As it is ubiquitous, anti-mucin responses have the potential for inducing autoimmune diseases against any of the normal tissues.

Surprisingly, when conducting investigations with peptides developed to bind with anti-Galα(1,3)Gal antibodies in relation to the problem of hyperacute xenograft rejection, it was found by the present inventors that the human mucin peptides (arising from muc1–muc4 genes, listed as muc pep 1–11 in table 1) also bound to the anti-Galα(1,3)Gal antibody (see co-pending international patent application filed on Sep. 27, 1996, also based on Australian Patent Application No. PN 5680/95). Given that the peptides developed to bind to anti-Galα(1,3)Gal antibodies exhibit similar antibody binding characteristics to the human mucin peptides, it was postulated that such peptides could be useful in generating an immune response against tumour antigens. Being non-self peptides this immune response has the potential to be greater than that generated by self peptides such as MUC1.

Accordingly therefore, it is an object of the present invention to develop novel cancer immunotherapy vaccines and methods of cancer therapy. Other objects of the present invention will become apparent from the following description thereof.

SUMMARY OF THE INVENTION

According to one embodiment of the present invention there is provided a cancer vaccine comprising a peptide which mimicks MUC1 or other cancer peptides and one or more pharmaceutically acceptable carrier or diluent, optionally in association with an appropriate carrier peptide or another therapeutic agent.

According to another embodiment of the present invention there is provided a method of treatment of a human patient suffering from or prone to suffer from cancer, which comprises administering to said patient an effective amount of a cancer vaccine comprising a peptide which mimicks MUC1 or other cancer peptides, and optionally one or more pharmaceutically acceptable carrier or diluent, optionally also in association with one or more appropriate carrier peptides or another therapeutic agents.

DETAILED DESCRIPTION OF THE INVENTION

It is to be recognised that throughout this specification, unless the context requires otherwise, the word "comprise", or variations thereof such as "comprises" or "comprising", will be understood to imply the inclusion of a stated element or integer or a group of elements or integers but not the exclusion of any other element or integer or group of elements or integers.

It was recognised by the inventors of the present application that α-galactosyl sugars such as d-galactose, melibiose, stachyose, methyl-α-d-galactopyranoside, D-galactosamine and derivatives thereof bind to anti-Galα (1,3)Gal antibodies. It was also noted by the present inventors that the Galα(1,3)Gal epitope is present on the surface of endothelial cells of animals other than higher primates (humans and old world monkeys). Higher primates do not make Galα(1,3)Gal as they lack a functional α(1,3) galactosyl transferase due to the presence of multiple in-phase stop codons and multiple insertions and deletions leading to frame shifts within the α(1,3)galactosyl transferase genes, which result in non-functional pseudo-genes (8,7). All humans however, have natural antibodies to Galα(1,3)Gal (15,18), which is probably due to immiunisation with bacteria which carry α-linked Gal as part of the lipopolysaccharide.

It is also known that the IB4 lectin which is a plant glycoprotein from the species *Griffonia simplicifolia*, is capable of binding to the Galα(1,3)Gal epitope. On this basis therefore, the present inventors proposed to locate peptides capable of binding to the anti-Galα(1,3)Gal antibody by screening peptides for binding with the IB4 lectin. A multitude of random amino acid sequence octapeptides was synthesised and displayed in a phage display library and screened for binding activity against the IB4 lectin, the surprising result of which was that a number of synthesised peptides demonstrated binding with the IB4 lectin. Similarly, other known peptides were also screened for binding against the IB4 lectin and it was surprisingly also found that the IB4 lectin bound to the protein core of the human mucin peptides (MUC 1–7) which are highly expressed on the surface of tumour cells (2,19) and which in this situation have an altered pattern of glycosylation which leads to exposure of the protein core (3). It has since been demonstrated by the present inventors that the IB4 binding synthetic peptides (Gal pep 1 to Gal pep 7) obtained from the random peptide library and the mucin peptides both bind to the anti-Galα(1,3)Gal antibody, and can be utilised in cancer therapy protocols.

The phrase within the specification peptides "mimicks MUC1 or other cancer peptides" encompasses all peptides which demonstrate analogous binding in the groove of class I MHC molecules. An indicator of mimicking MUC1 is binding to IB4 or anti-Galα(1,3)Gal antibodies. Relative affinities of peptides for the anti-Galα(1,3)Gal antibody or for IB4 can be calculated by comparing the molar concentration required to obtain 50% inhibition of the binding of antibody by lectin or sugars, using an ELISA (enzyrme-linked immunosorbent assay). The details of this technique will be described more fully in the examples under the heading "materials and methods". The peptides of the invention include peptides having only as few as 3 amino acids up to polypeptides including up to or exceeding 200 amino acids. Although, as will be discussed in further detail, preferred peptides of the invention include the consensus is sequence ArXXArZ (as defined below) and the peptides Gal pep 1 to Gal pep 7 (SEQ ID Nos. 1–7, respectably), this is in no way to be considered limiting upon the invention. Other peptides which demonstrate the requisite cancer peptide mimicking, and particularly peptides which are similar to Gal pep 1–Gal pep 7 (SEQ ID Nos. 1–7, respectably) but which include one or more deletions or modifications to the amino acid sequence are to be considered to fall within the scope of the invention.

Although not to be considered limiting upon the scope of the invention, it is noted that the peptides exhibiting antibody binding characteristics which were located from the random amino acid library screening have the following consensus sequence:

ArXXArZ where Ar=tryptophan (W), phenylalanine (F) or tyrosine (Y)
X=a small aliphatic or polar amino acid residue such as for example glutamic acid O), serine (S) aspartic acid (D), glycine (G), isoleucine (I), alanine (A) or asparagine (N).
Z=branched aliphatic amino acid such as for example valine (V) isoleucine (I), or leucine (L).

Particularly preferred are the peptides shown in FIG. 1 as Gal pep 1 to Gal pep 7 (SEQ ID Nos. 1–7, respectably) which each conform with the above consensus sequence.

Other preferred compounds are the mucin glycopeptides MUC 1 to MUC 7 (4).

The most preferred peptide however, is Gal pep 1 which has the sequence DAHWESWL (SEQ ID No. 1), and which can mimic the conformation of the MUC1 VNTR peptides SAPDTRPAP/APDTRPAPG (SEQ ID No. 9/SEQ ID No. 10) (which bind H-2D$^d$ and H-2L$^d$ respectively).

The applicants have previously shown that mice immunised with mannan-MUC1-peptides make cytotoxic T cells (CTLs), little antibody and are protected from MUC1$^+$ tumour growth. The same specific anti-MUC1 responses can be produced by immunising with the peptides of the invention and particularly the DAHWESWL peptide (SEQ ID No. 1) linked to KLH, in that aniti-MUC1 (and anti-DAHWESWL) CTL responses can be induced or antibody produced and more particularly, specific tumour protection occurs of magnitude greater than or similar to that obtained with mannan-MUC1 peptide immunisation.

It is also possible that the peptides as outlined above which accord with the present invention can be conjugated to other species. The other species comprehended include all chemical species which can be fused to the peptide in question without affecting the binding of the peptide by T-cells. Specific examples are for example other antigens which may elicit a separate immune response, carrier molecules which may aid absorption or protect the peptide concerned from enzyme action in order to improve the effective half life of the peptide. Other possibilities are conjugation of peptides to solid or liquid phases for use in immuno assays for diagnostic or therapeutic purposes. Specific examples of peptide conjugation are conjugation to other serum proteins or macromolecules.

The present invention relates to methods of cancer therapy which involve the peptides according to the present invention. In particular vaccines which include peptides according to the invention can be administered to cancer patients to induce immunity to the mucin core of aberrantly glycosylated mucins which are highly expressed on the surface of tumour cells. Mucins are expressed in adenocarcinomas in cancer of the breast, liver, colon, prostate and others. In treating cancer it may useful to conjugate peptides to other carriers to induce T cells capable of recognising and destroying cancer cells.

The present invention also relates to methods of vaccinating human subjects as a method of cancer therapy or treatment for auto-immune disease. In this way the inventive vaccine can be administered to human patients who are either suffering from, or prone to suffer from cancer or autoimmune disease.

In cancer therapy it is possible to immunise with peptide-carrier combination to induce T cells capable of recognising and destroying target cancer cells or alternatively immunisation to induce antibodies with anti-tumour activity.

The vaccine according to the invention may contain a single peptide according to the invention or a range of peptides which cover different or similar pepitopes. In addition or alternatively, a single polypeptide may be provided with multiple epitopes. The latter type of vaccine is referred to as a polyvalent vaccine.

In a preferred embodiment of the invention the peptide is conjugated to a carrier protein such as for example tetanus toxoid, diphtheria toxoid or oxidised KLH in order to stimulate T cell help.

The formation of vaccines is generally known in the art and reference can conveniently be made to Remington's Pharmaceutical Sciences, 17th ed., Mack Publishing Co., Easton, Pa., USA.

For example, from about 0.05 ug to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendrite cells sensitised in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in th e appropriate solvent with various of the other ingr edients enumerated above, as required, followed by filtered sterliation. Generally, dispersions are prepared by incorporating the various sterided active ingredient into a sterile vehicle which contains the basic dispersion medium and the required other ingredients from those enumerated above. In the case of sterile powders for the p reparation of sterile injectable solutions, t he preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, waftes, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 ug and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 $\mu$g to about 2000 mg. Expressed in proportions, the active compound is generally present in from about 0.5 $\mu$g/ml of carrier. In the case of compositions containing supplementary active ingredients, the dosages are determined by reference to the usual dose and manner of administration of the said ingredients.

Still another aspect of the present invention is directed to antibodies to the peptides. Such antibodies may be monoclonal or polyclonal and may be selected from naturally occurring antibodies to the peptide or may be specifically raised to the peptides. In the case of the latter, the peptides may need first to be associated with a carrier molecule. The antibodies and/or peptides of the present invention are particularly useful for immunotherapy and vaccination and may also be used as a diagnostic tool for infection or for monitoring the progress of a vaccination or therapeutic regime.

In another aspect of the invention there are provided nucleotide sequences encoding the proteins according to the present invention. Preferably the nucleotide sequence encodes Gal pep 1.

Nucleotide sequences may be in the form of DNA, RNA or mixtures thereof. Nucleotide sequences or isolated nucleic acids may be inserted into replicating DNA, RNA or DNA/RNA vectors as are well known in the art, such as plasmids, viral vectors, and the like (Sambrook et al, Molecular Cloning A Laboratory Manual, Coldspring Harbour Laboratory Press, NY, second edition 1989). Nucleotide sequences encoding the antibodies of the present invention may include promoters, enhances and other regulatory sequences necessary for expression, transcription and translation. Vectors encoding such sequences may include restriction enzyme sites for the insertion of additional genes and/or selection markers, as well as elements necessary for propagation and maintenance of vectors within cells.

Nucleotide sequences encoding antibodies according to the present invention may be used in homologous recombination techniques as are well known in the art Capecchi M R, Altering the Gene by Homologous Recombination, Science 244:1288–1292, 1989; Merleno G T, Transgenic Animals in Biomedical Research, FASEB J 5:2996-3-001, 1992; Cosgrove et al, Mice Lacking MAHC class II molecules, cell 66:1051–1066, 1991; Zijlstra et al, Germ-Line Transmission of a Disrupted B2-Microglobulin Gene Produced by Homologous Recombination in Embryonic Stem Cells, Nature 342:435, 1989). In such techniques, nucleotide sequences encoding the peptides according to the invention are recombined with genomic sequences in stem cells, ova or newly fertilised cells comprising from 1 to about 500 cells. Nucleotide sequences utilised in homologous recombination may be in the form of isolated nucleic sequences or in the context of vectors. Insertion of new active genes by transgenesis is also comprehended.

The present invention will now be described with reference to the following non-limiting figures and examples.

IN THE FIGURES

FIG. 1. Amino acid sequences Gal pep 1 to Gal pep 7 peptides (SEQ ID Nos. 1–7, respectively) of phage isolated by panning with the IB4 lectin. Amino acid sequences were deducted from the DNA sequence encoding the amino-terminal octapeptide of pIII from phage eluted from IB4 lectin with 200 mM α-methyl galacyoside.

FIGS. 2(A–B). Peptide inhibition of hemagglutination. Varying concentrations of Gal pep 1 (SEQ ID No. 1) (○) or CD48 pep 1 (SEQ ID No. 11) (◆) (shown in mM on horizontal axis) were examined in a hemagglutination assay using pig RBC as targets and either (A) IB4 lectin (1 µg/ml) or (B) NHS (final dilution of 1/32).

FIGS. 3(A–C). Cytofluorographic analsysis of inhibition produced by Gal pep 1 (SEQ ID No. 1). (A); Staining of PIEC cells with IB4 lectin (1 µg/ml). (B) Staining of PIEC cells with NHS (final dilution of 1/50) and anti-human Ig. (C) Staining of PBL with IB4 lectin (µg/ml). Peptides were used at 5 mM (A and C) or at 20 mM (B). In each panel profile "a" represents binding in the presence of Gal pep 1 (SEQ ID No. 1), and profile "b" the binding in the presence of CD48 pep 1 (SEQ ID No. 11). The profile of binding without peptide, for both the IB4 lectin and NHS, was identical to profile "b" in each panel (not shown for clarity).

Figure 4:
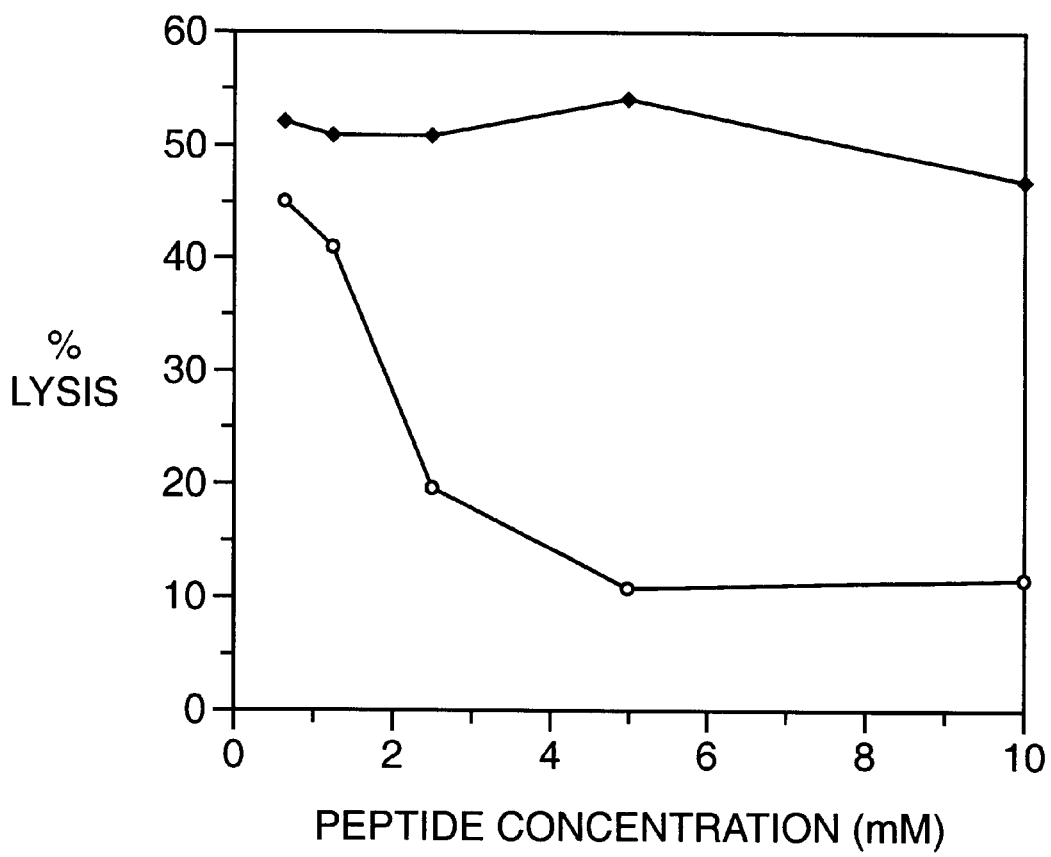

FIG. 4. Inhibition of cytotoxicity due to natural antibody and complement by Gal pep 1 (SEQ ID No. 1). Varying concentrations of Gal pep 1 (○) or CD48 pep 1 (◆) (shown in mM on horizontal axis) were examined in a cytotoxicity assay using NHS (final dilution of 1/25) and PEEC cells as targets. Vertical axis shows % lysis; cells were <95% viable and complement control was <10%.

FIGS. 5(A–D). Inhibition of binding of IB4 lectin and anti-Galα(1,3)Gal IgG to Galα(1,3)Gal-BSA by oligosaccharides or peptides. Varying concentrations of inhibitors (shown in mM on horizontal axis) were examined in an Elisa for inhibition of IB4 (16 µg/ml) (A, B) or anti-Galα(1,3)Gal IgG antibodies (75 µg/ml) (C,D). Inhibitors used: oligosaccharides—glucose (◆), Galα(1,3)Gal (○) and melibiose (●) (A and C); peptides—Gal pep 1 (SEQ ID No. 1) (○) or CD48 pep 1 (SEQ ID No. 11) (◆) (B and D). Vertical axis shows OD at 405 nm.

FIGS. 6(A–B). Peptide inhibition of IB4 lectin binding to pig endothelial cells. Varying concentrations of peptides (shown in mM on horizontal axis) were explained for ability to inhibit the binding of IB4 lectin (1 µg/ml) to tie PIEC cells using cytofluorographic analysis. (a) Gal pep 1 (SEQ ID No. 1) (□), Muc pep 1 (SEQ ID No. 15) (○). (b) Muc pep 2 (SEQ ID No. 16) (□), Muc pep 3 (SEQ ID No. 17) (□), Muc pep 4 (SEQ ID No. 18) (○), Muc pep 5 (SEQ ID No. 19) (●).

Figure 7:
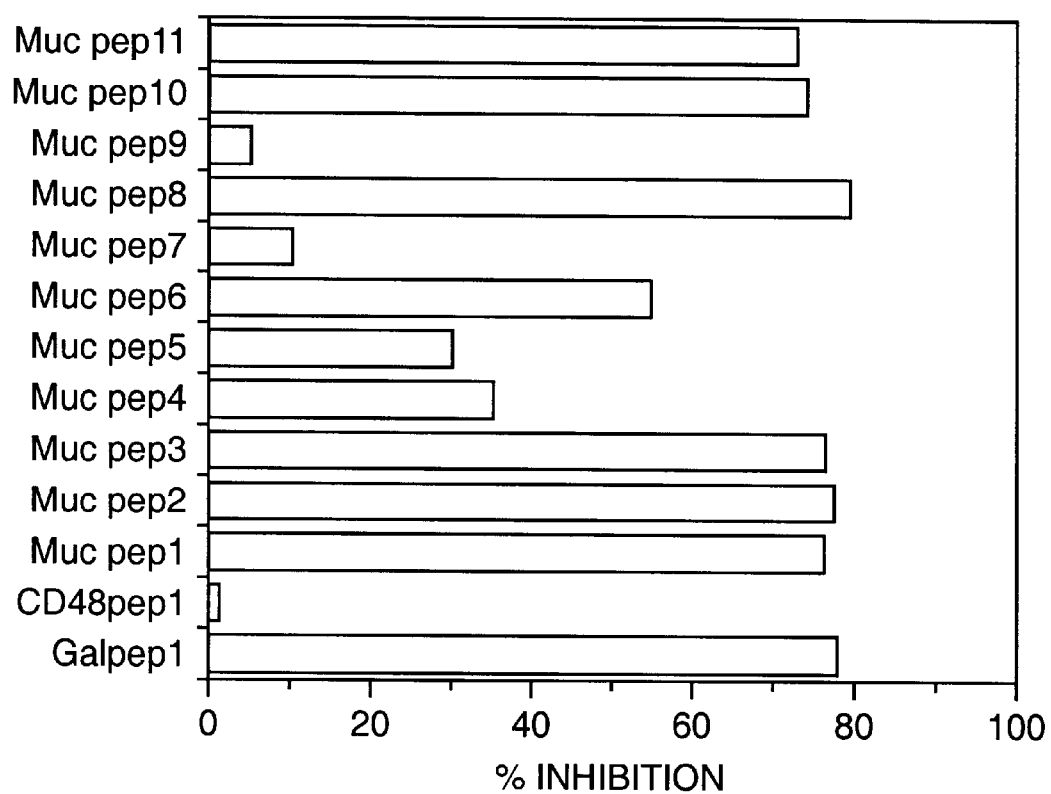

FIG. 7. Inhibition of IB4 lectin binding to pigendothelial cells by mucin peptides. All peptides used at 5 mM, using cytofluorograhic analysis. Inhibition calculated relative to no peptide control.

FIGS. 8(A–B). Inhibition of binding IB4 lectin and anti-Galα(1,3)Gal IgG to Galα(1,3)Gal-BSA by mucin peptides. Peptides at 5 mM were examined in an Elisa for inhibition of IB4 (16 µg/ml) (a) or anti-Galα(1,3)Gal IgG antibodies (75 µg/ml) (b). Vertical axis shows peptides used, horizontal axis shows OD at 405 nm.

Figure 9:
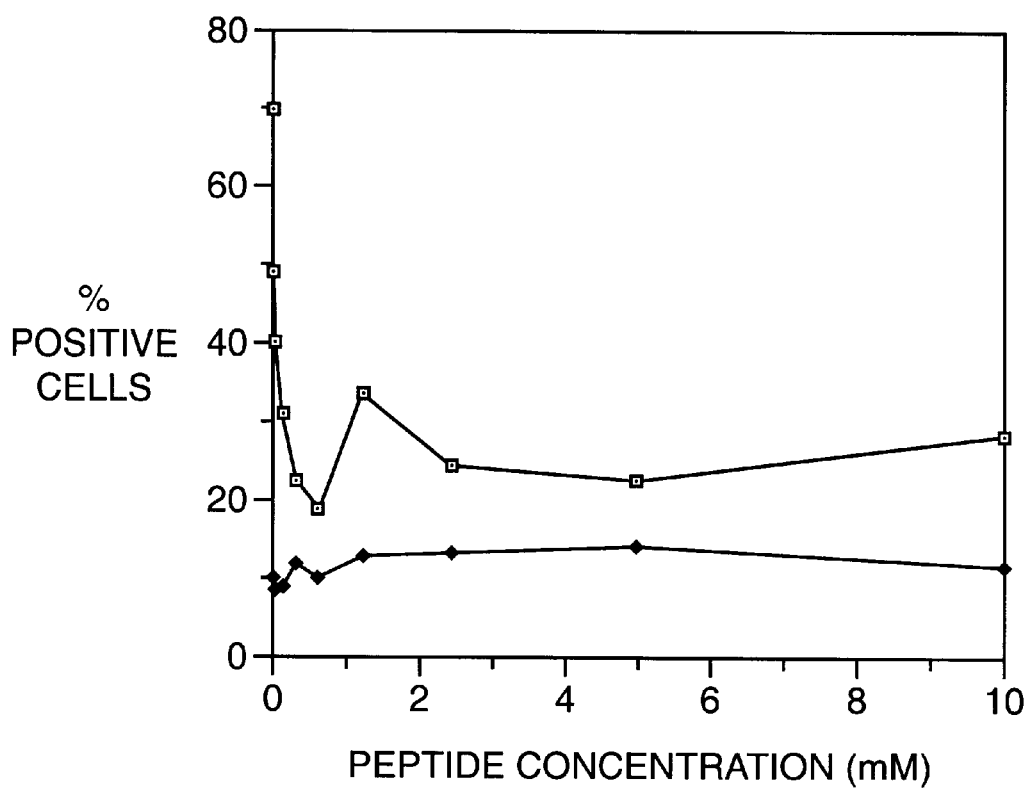

FIG. 9. Inhibition of anti-MUC1 mAb by Gal pep 1. Varying concentrations of peptides (shown in mM on horizontal axis) were examined for ability to inhibit the binding of anti-MUC1 mAb to MOR5 cells using the cytoflurograph. Peptides used: Gal pep 1 (SEQ ID No. 1) (□), Muc pep 1 (SEQ ID No. 15) (◆).

Figure 10:
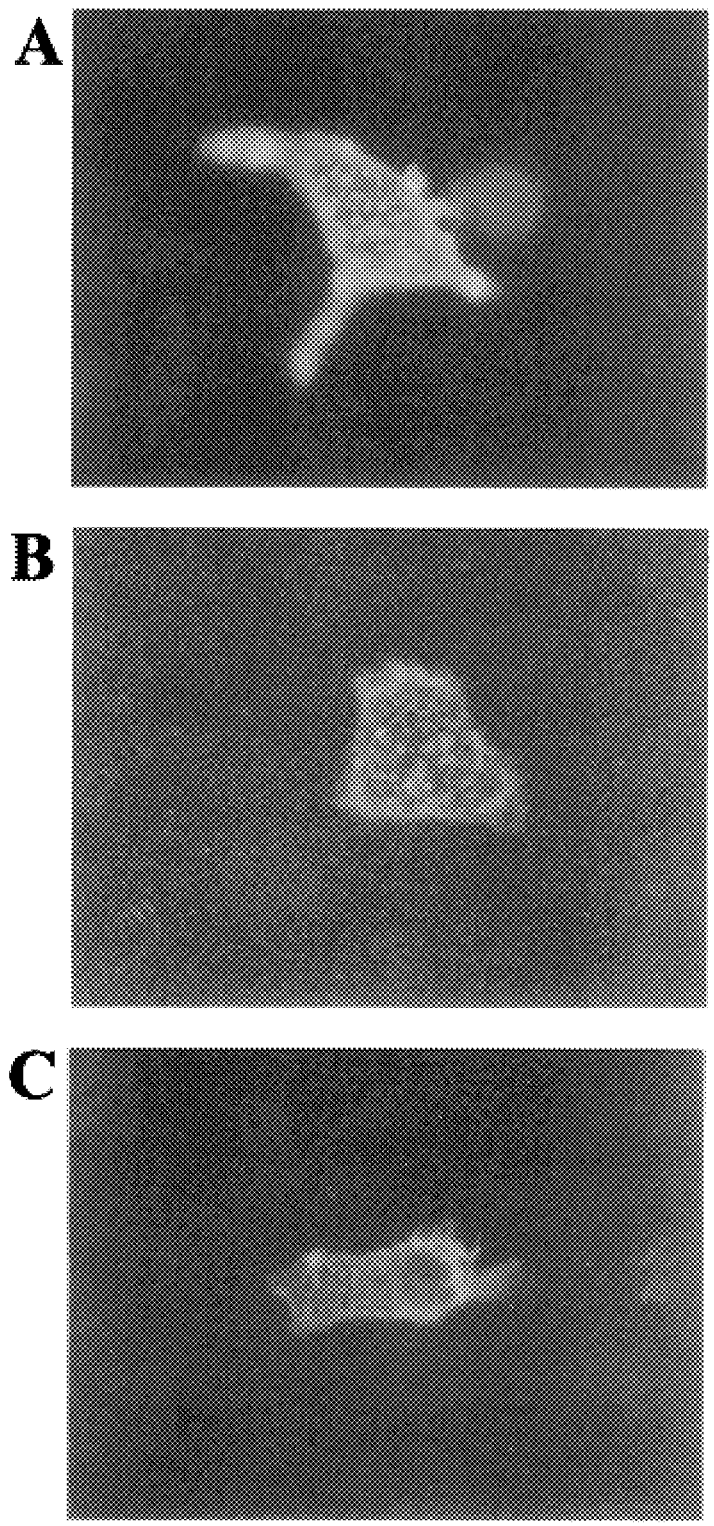

FIGS. 10(A–C). Cell surface staining of COS cell transfection with MUC1 cDNA clone. (A) stained with VA1 mAb. (B) stained with 3E1.2 mAb. (C) stained with IB4 lectin.

Figure 11:
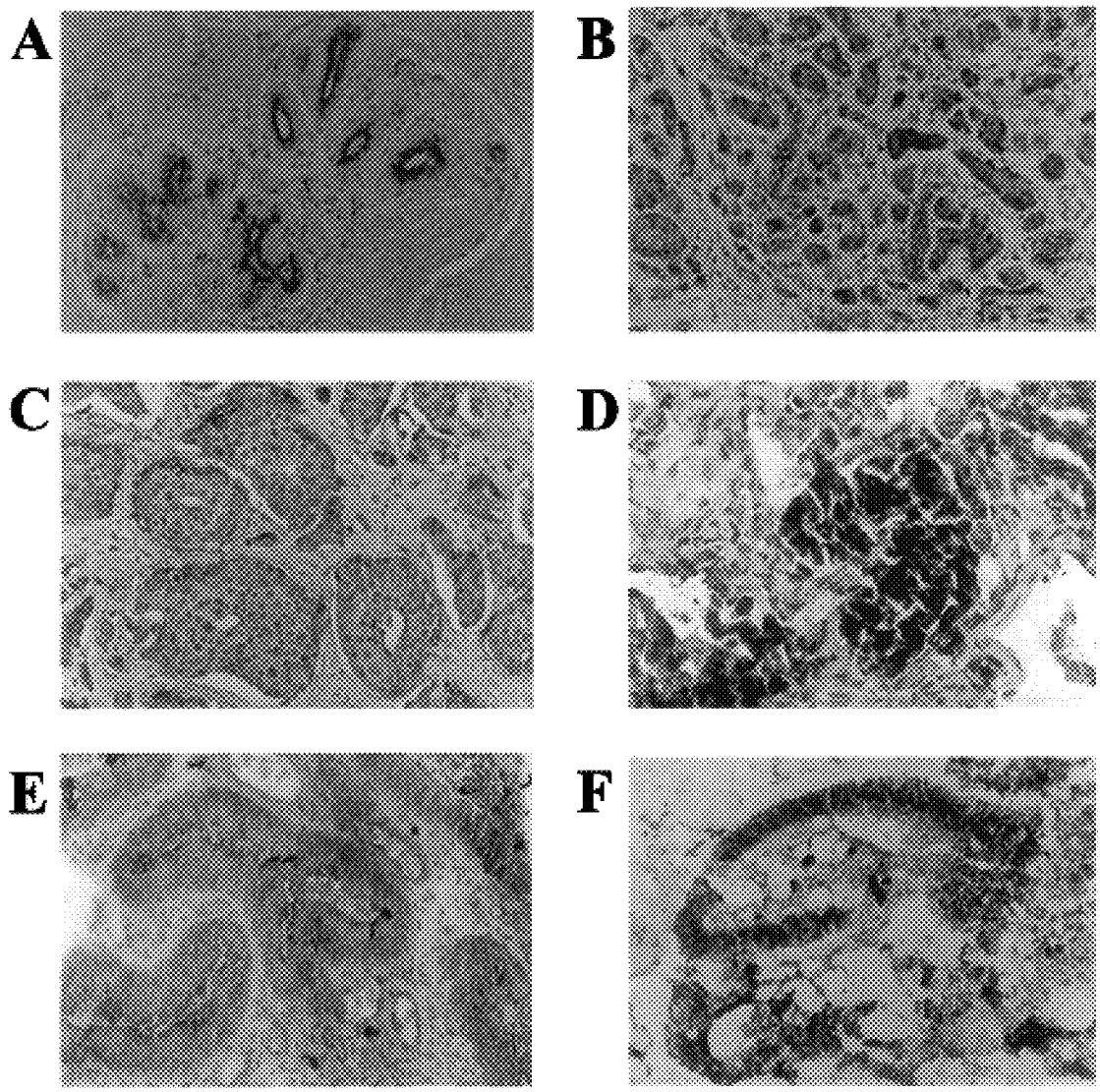

FIGS. 11(A–F). Histological analsysis of malignant human tissue with IB4 lectin. Biotinylated IB4 lectin was used in an immunoperoxidase staining on formalin fixed and paraffin embedded tissue (A, B, C) or fresh frozen tissue (D,E,F). A: normal breast. B: moderately differentiated infiltrating breast carcinoma. D: poorly differentiated infiltrating breast carcinoma. E: moderately differentiated infiltrating breast carcinoma. F: adenocarcinoma of the colon. Original magnification×200.

Figure 12A:
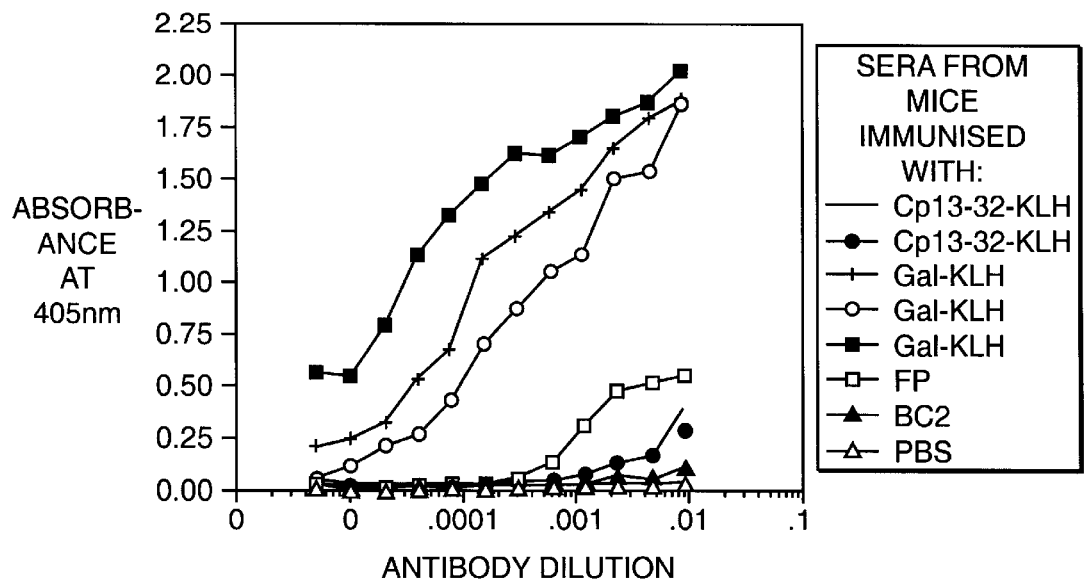
Figure 12B:
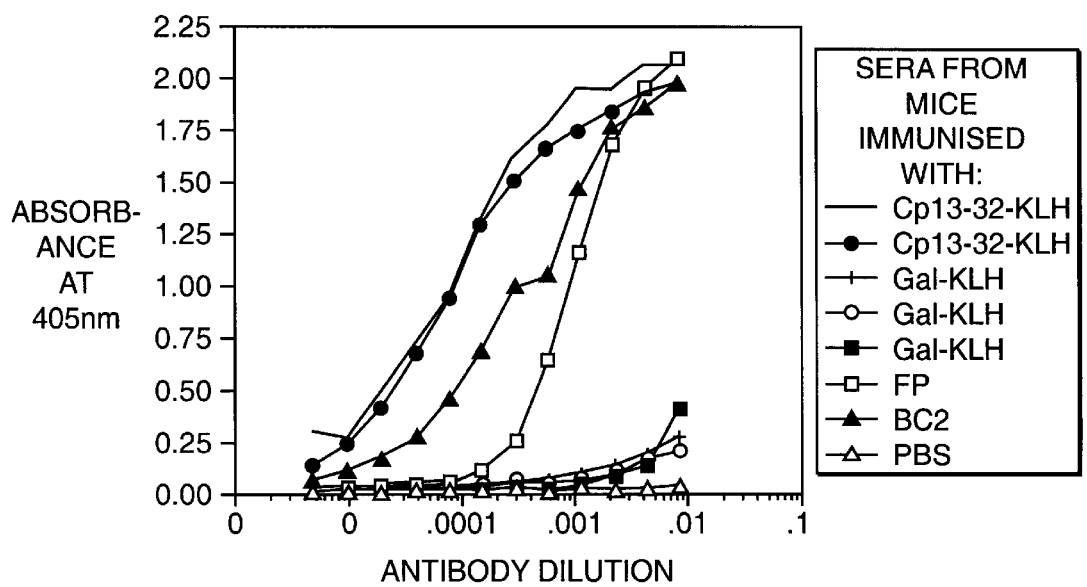

FIGS. 12A & 12B Antibody titres in mice immunised with various preparations (see Figure) and tested on Gal peptide coated plate (FIG. 12A) or on MUC1-peptide (CP$^{13}$-32 peptide) coated plate (FIG. 12B).

Figure 13:
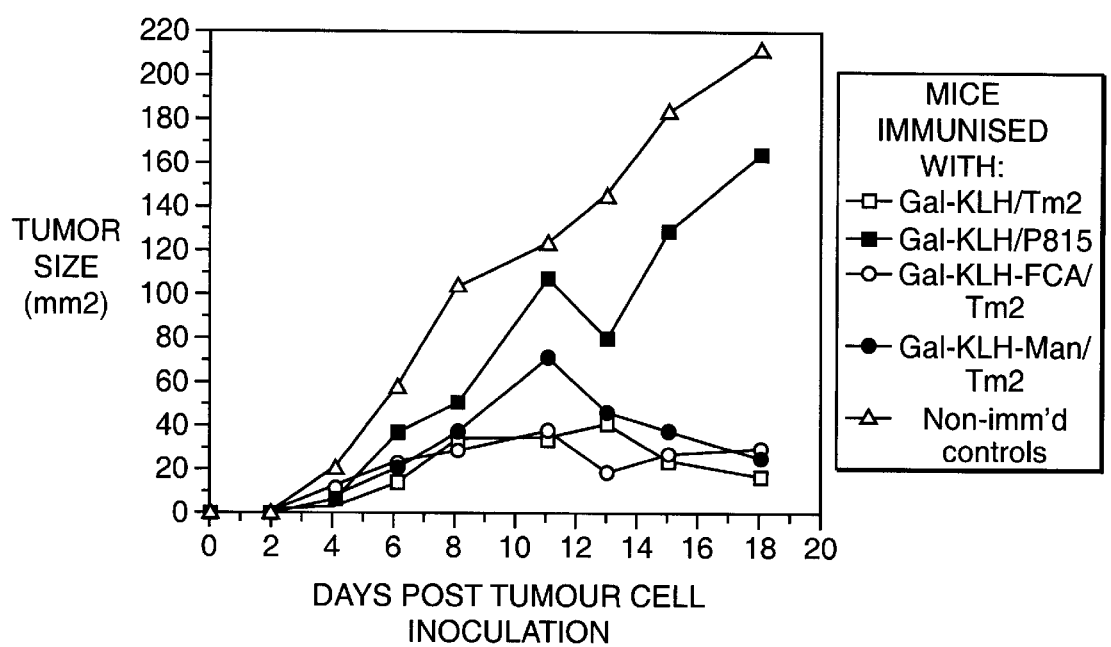

FIG. 13 DBA 2$^{++}$ mice were irnmunised three times intraperitoneally and mice were challenged with p815

MUC1+ on P815 tumour cells. Mice immunised with Gal-KLH, Gal-KLH-FCA and Gal-KLH-mannan and challenged with p815 MUC1+.

Figure 14A:
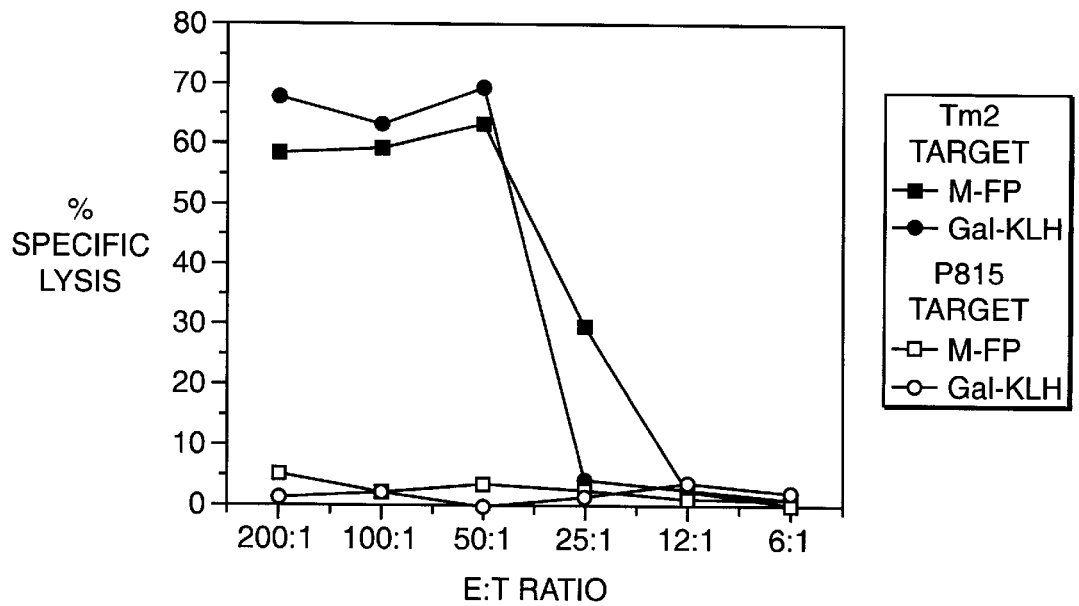
Figure 14B:
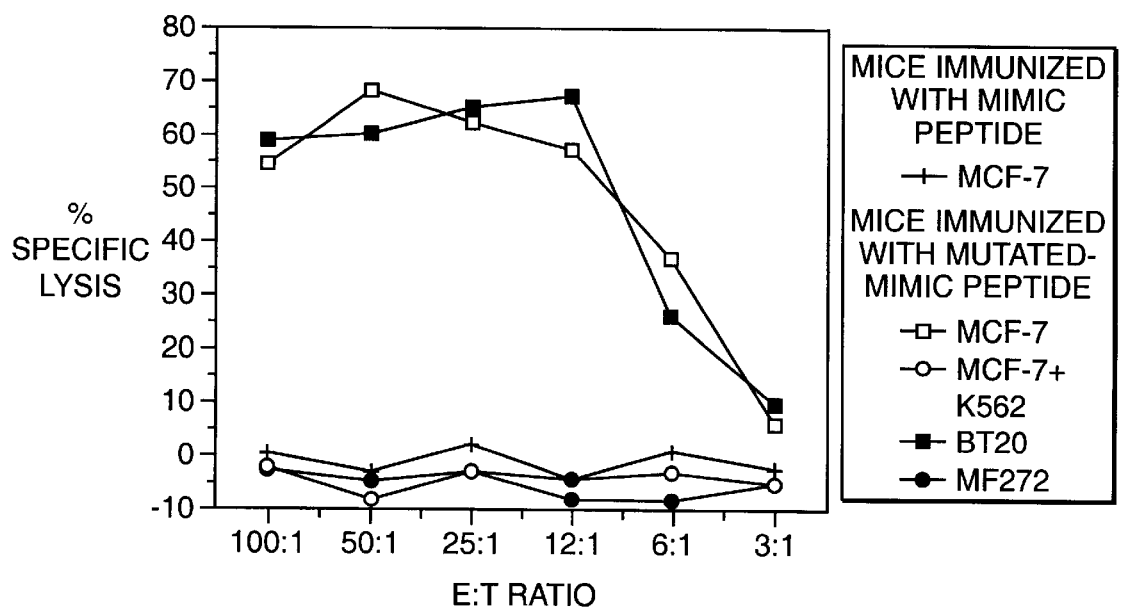

FIG. 14(A) Direct CTL assay using p815 MUC1+ (Tm2) or P815 targets. DBA/2 mice were immunised with MFP, or Gal-KLH. FIG. 14(B) CTL assay using HLA-A*0201/$K^b$ spleen CTLs from mice immunised with either mimic or mutated mimic peptides on $^{51}$Cr MCF-7 (MUC1+HLA-A*0201+) cells. $^{51}$CrBT20 (MUC1+HLA-A*0201-) or MF272 (MUC1-IILA-A*0201+) cells were also used as targets and as well as $^{51}$CrMCF-7 cells incubated with cold K562 cells at a 30:1 hot:cold ratio (K562, a myelogenous leukemia cell line). Vertical axis=% lysis; horizontal axis= E:T ratio.

Figure 15:
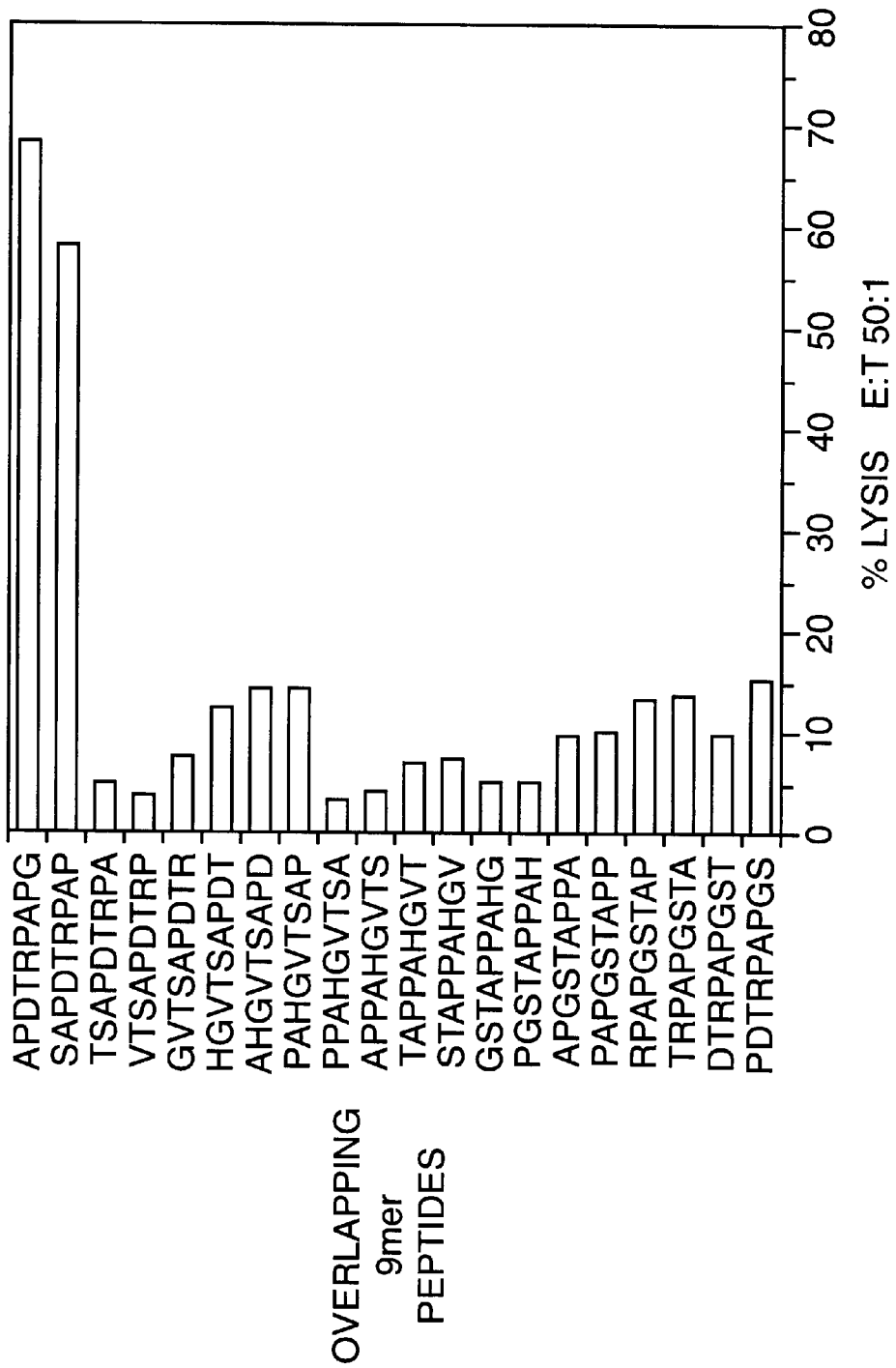

FIG. 15 CTL-assay using CTLs from DBA/2 Gal-KLH immunised mice on peptide (overlapping 9-mers spanning the MUC1 VNTR) pulsed P815 target cells.

Figure 16:
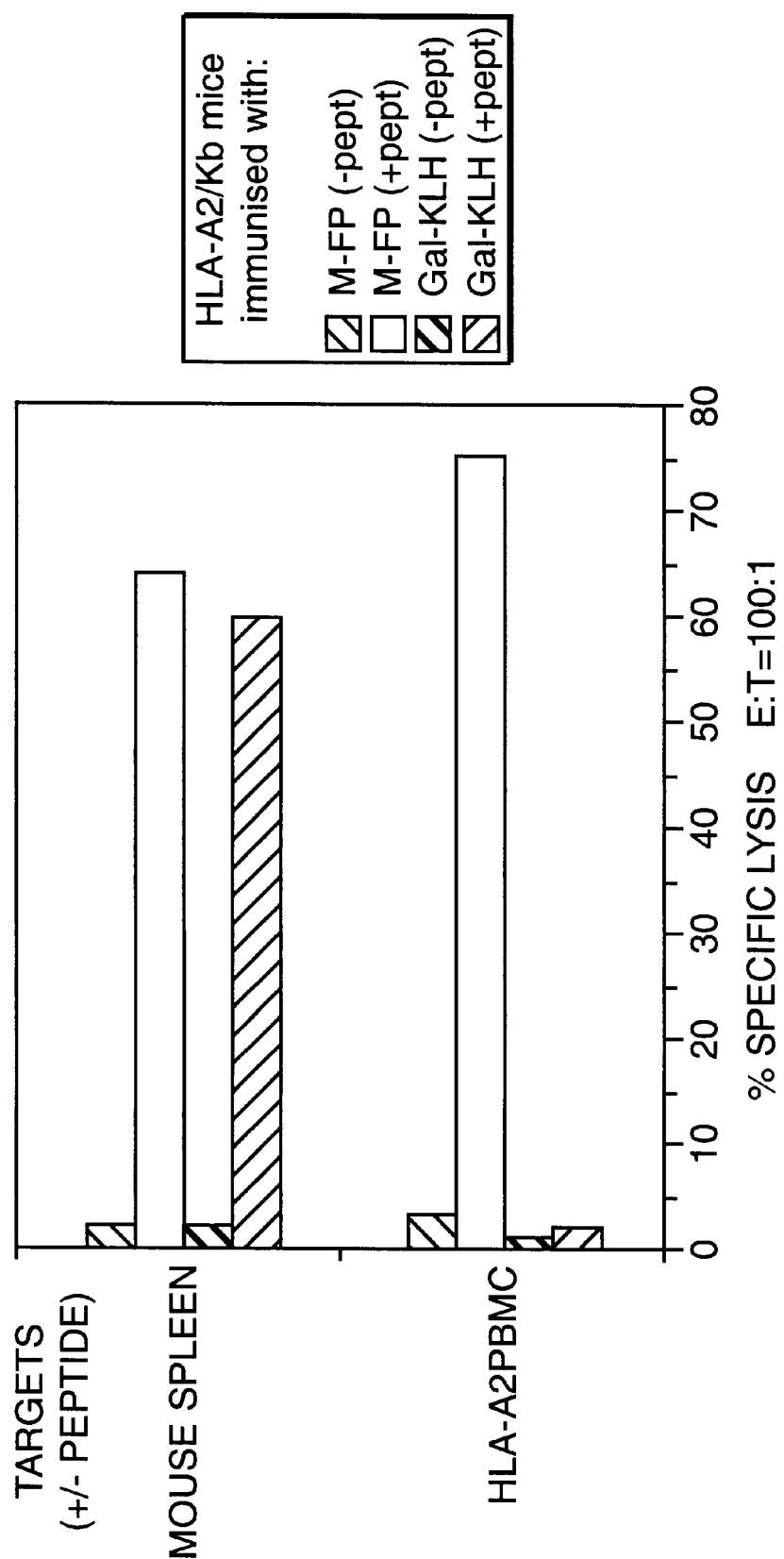

FIG. 16 CTL assay using CTLs from HLA-A2/$K^b$ immunised mice with MFP or Gal-KLH Target cells were either autologous spleen pHA-blast peptide (MUC1) at pulsed cells or HLA-A2 pHA-blast PBMC peptide (MUC1) pulsed.

Figure 17:
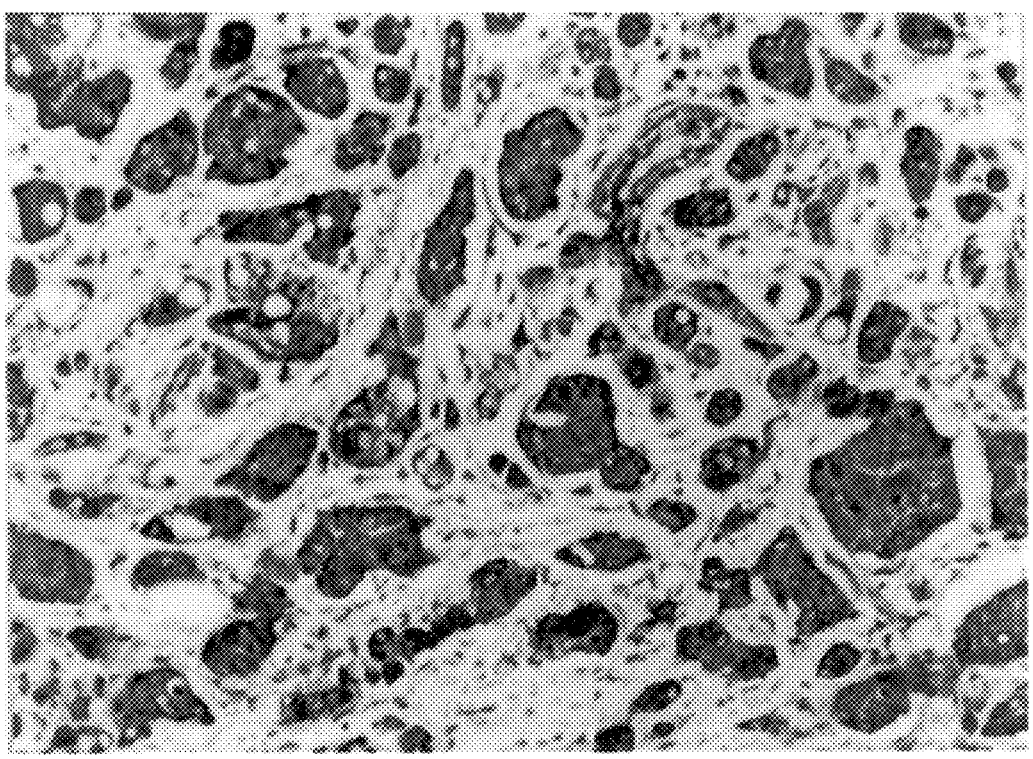
Figure 17:
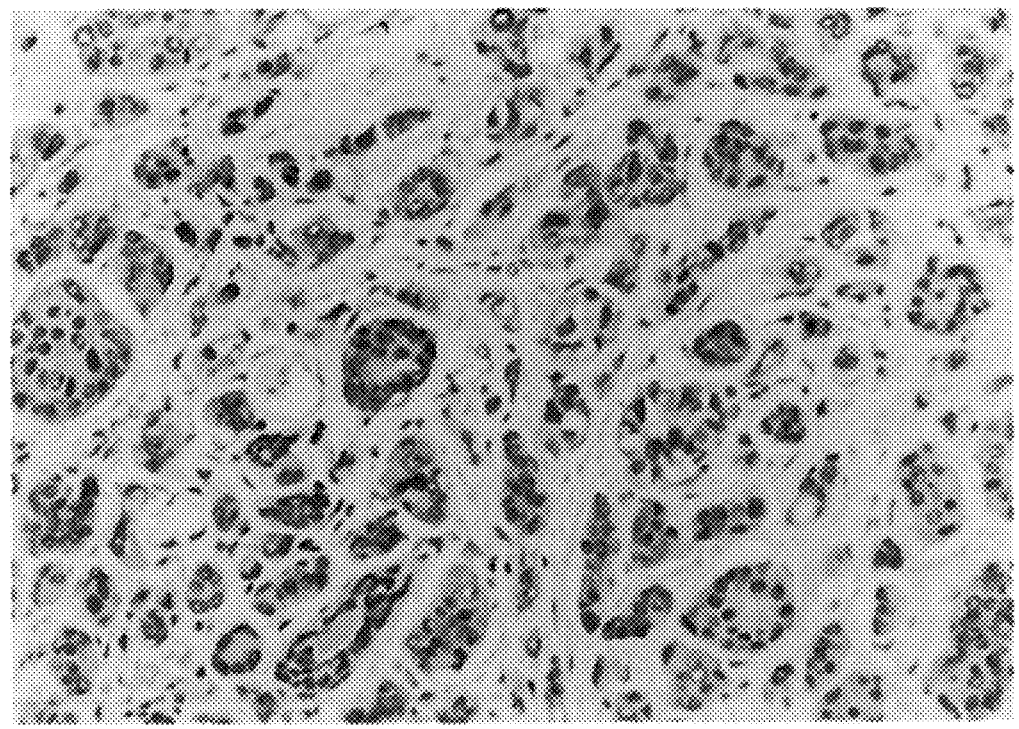

FIGS. 17(A–B) Histological analysis of malignant human tissue with anti-Galα(1,3)Gal antibodies. Human anti-Galα (1,3)Gal antibodies used in an immunoperoxidase staining on formalin fixed and paraffin embedded tissue (A), and tested with human serum depleted of anti-Gal(1,3)Gal antibodies (B).

EXAMPLE 1

RECOGNITION OF PEPTIDES BY ANTI-GALA (1,3)GAL ANTIBODIES

Materials and Methods

Isolation of Peptides from a Peptide Library

A random octamer library was constructed and screened by affinity purification [12] using the IB4 lectin (Sigman, St. Louis, Mo.) from *Griffonia simplicifolia*, which binds to bind to the Galα(1,3)Gal [5]. After three rounds of screening phage clones that displayed specific binding to IB4 were amplified and their DNA sequenced.

Cells

The pig endothelial cell line, PIEC, was obtained from Dr, Ken Welsh (Churchill Hospital, Oxford, UK). Peripheral blood lymphocytes (PBL) and erythrocytes (RBC) were obtained from fresh pig blood [14].

Synthesis of Peptides

Peptides were synthesised using an Applied Biosystems Model 430A automated synthesiser (Foster City, Calif.), based on the standard Merrifield solid phase synthesis method [ii], and were purified (to >90%) by reversed phase high performance liquid phase chromatography (Waters Associates, Milford, Mass.) on a C-8 quapore RP-300 column using a gradient solvent system of 0.1% aqueous trifluoroacetic acid/acetonitrile. All reagents for synthesis were purchased from Applied Biosystems.

Reagents

Normal human serum (NIIS) was obtained from 10 health volunteers, pooled and heat inactivated at 56° C. for 30 minutes before use. Human anti-Galα(1,3)Gal IgG antibodies were purified from the NHS by firstly fractionation on a Protein G sepharose column (Pharmacia I.KB Biotechnololgy, Uppsala, Sweden), followed by affinity chromatography on Galα(1,3)Galβ(1,4)GluNAc conjugated glass beads (Syntesome, Princeton, N.J.). FITC conjugated sheep anti-human IgM, sheep anti-mouse IgG and Horse radish peroxidase (HRP) conjugated sheep anti-human IgM or IgG were obtained from Silenus (Melbourne, Australia).

HRP conjugated streptavidin was obtained from Amersham International (Amersham, UK). The anti-CD48 monoclonal antibody was produced at the Austin Research Institute [20]. The IB4 lectin was labelled with FITC or biotin [14,9]. Melibiose [Galaα(1,6)Glc] and glucose were obtained from Sigma, and Galα(1,3)Gal, either free or coupled to BSA, was obtained from Dextra Laboratories (Reading, UK).

Serology

The binding of lectin or antibody to the surface of pig cells was detected by hemagglutination [14], cytotoxicity [21] or flow cytometry [14] using the FACSCAN flow cytometer (Becton Dickinson, Mountain View, Calif.).

Elisa

Relative affinities of the sugars or the peptides, for both IB4 lectin and human natural antibodies were calculated by comparing the molar concentration required to obtain 50% inhibition of the binding of antibody or lectin by sugars or peptides, using an ELISA: 50 µl of Galα(1,3)Gal-BSA (Dectra Laboratories) at a concentration of 10 µg/ml in 0.2M carbonate buffer pH 9.6 were added to the wells of an ELISA plate (Greiner, Frickenhausen, Germany), incubated at 37° C. for 2 hours under humidifying conditions and non-specific binding sites were blocked with 2% BSA for 1 hour at 37° C. 50 µl of either purified anti-Galα(1,3)Ga IgG or biotinylated IB4 lectin was added to the wells, incubated for 45 minutes at 22° C., washed with PBS-0.05% Tween 20, and 50 µl of the relevant IIRP conjugate added and incubated for a further 45 minutes before washing and the addition of 50 µl of substrate (2,2' Azino-di-B-ethylbenzthiozoline (Zymed, San Francisco, Calif.)) and reading the $OD_{405}$.

Results

Isolation of Peptides that Bind IB4 Lectin

The peptide library, consisting of $1.4 \times 10^9$ independent recombinant phage, was screened in three cycles of panning, elution and amplification against immobilised IB4. After the third cycle of panning, 9 randomly selected phage isolates displayed specific IB4 binding. The DNA from these clones was sequenced and the deduced peptide sequences are shown in FIG. 1 (N.B. one sequence, DGHWDSWL (SEQ ID No. 5), appeared in three separate phage isolates). These peptides have the consensus sequence ArXXArZ, where Ar=W, F or Y, X is a small aliphatic or polar residue and Z is a branched aliphatic amino acid. One of these sequences, DAHWESWL (Gal pep 1) (SEQ ID No. 1), was synthesised for further studies and found to inhibit, by 50%, IB4 reaction with galactomannan (from *Cassia alata*) at a concentration of 5 mM (not shown).

Peptide Blocking of IB4 Lectin and NHS Hemagglutination of Pig RBC

Figure 2B:
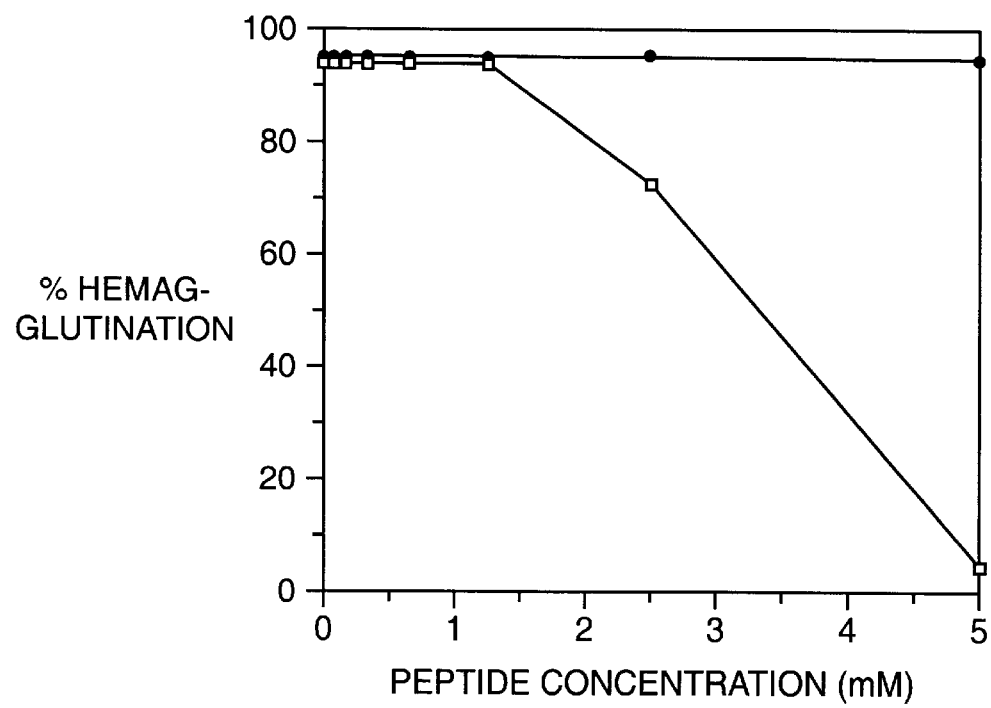

Inhibition of hemagglutination of pig RBC by IB4 using Gal pep 1 (SEQ ID No. 1) was consistently observed (FIG. 2): complete inhibition of IB4 induced hemagglutination was observed using Gal pep 1 in the range of 5 mM to 0.156 mM, with no inhibition using the control peptide CD48 pep 1 (YTFDQKIVEWDSRKSKC) (SEQ ID No. 11) (FIG. 2A). Similarly, partial blocking of hemagglutination using NHS was observed with 5 mM Gal pep 1 but not CD48 pep 1 (FIG. 2B).

Figure 3A:
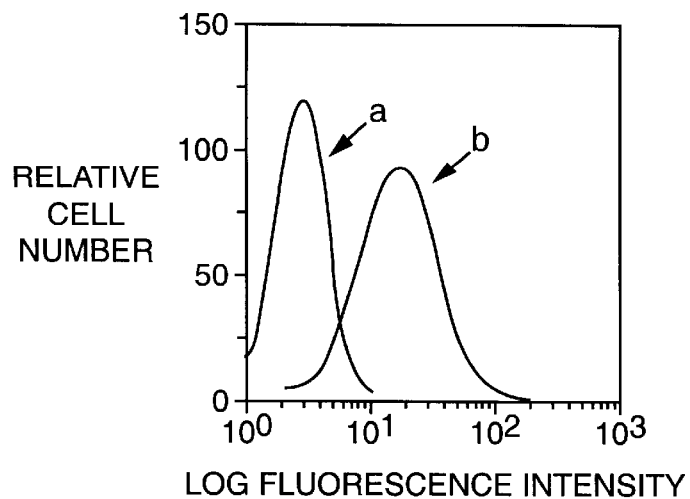
Figure 3B:
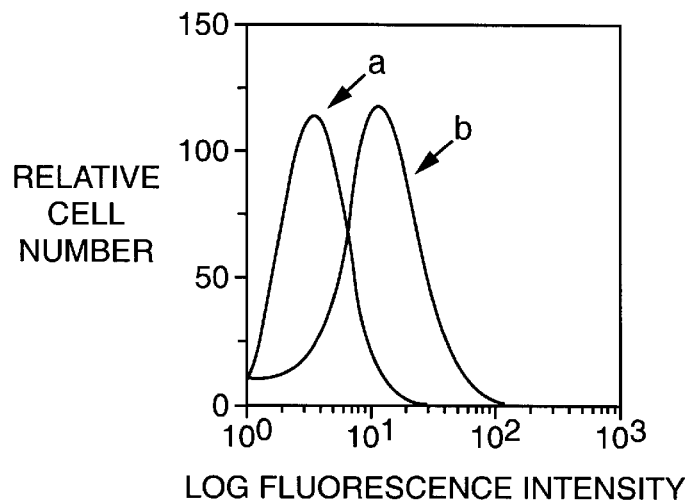
Figure 3C:
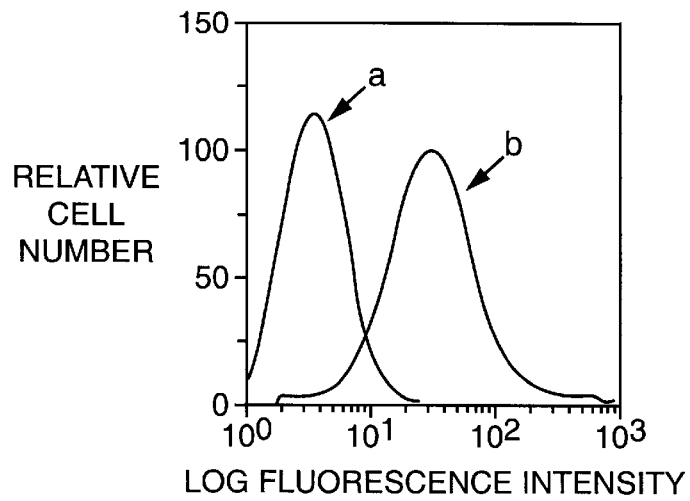

Peptide Blocking of the Binding of IB4 Lectin and NHS to Pig Endothelial Cells and Lymphocytes Peptides were tested for inhibition of binding of IB4 to PIEC and pig PBL; Gal pep 1 (SEQ ID No. 1) completely inhibited the binding of IB4 to PIEC in the range of 5 mM (FIG. 3A) to 0.625 mM (now shown). The Gal pep 1 was then used to block the binding of human natural antibodies to PIEC: inhibition occurred at a concentration of 20 mm (FIG. 3b). But not when used at lower concentrations (data not shown). No inhibition was observed using CD48 pep 1 (SEQ ID No. 11) at a concentration of 20 mM (FIGS. 3A & B). Gal pep 1 also blocked the binding of IB4 with PBL at a peptide concentration of 5 mM (FIG. 3C), whereas the control peptide had no effect. The specificity of these reactions was shown as Gal pep 1 had no effect on the binding of anti-CD48 monoclonal antibody to human PBL (data not shown).

Peptide Blocking of the Cytotoxicity of NHS on Pig Endothelial Cells

Human cytotoxic antibodies directly damage pig endothelial cells in a pig-to-human xenograft, therefore the ability of Gal pep 1 (SEQ ID No. 1) to inhibit the cytotoxicity of human antibodies on PIEC in vitro was tested; Gal pep 1 inhibited the cytotoxicity of NHS (10 mM to 2.5 mM), whereas CD48 pep 1 (SEQ ID No. 11) had no effect (FIG. 4).

Relative "affinities" of Gal pep 1 and α-galactosyl Sugars for IB4 Lectin or Anti-Galα(1,3)Gal Antibodies An Elisa was established to calculate the relative "affinity" of the Gal pep 1 (SEQ ID No. 1) for the IB4 lectin and for human anti-Galα(1,3)Gal antibodies, and to compare these with the affinities for α-galactosyl sugars. Biotinylated IB4 lectin and purified anti-Galα(1,3)Gal IgG antibodies were titered on Galα(1,3)Gal-BSA, and for the blocking experiments were used at two dilutions less than that required to give 50% of the maximum $OD_{405}$ reading. The results of inhibition of either the IB4 lectin or pure anti-Galα(1,3)Gal IgG antibodies with glucose, melibiose, Galα(1,3)Gal or Gal pep 1 are shown in FIG. 5; the IB4 lectin (FIGS. 5A & B) or pure anti-Galα(1,3)Gal IgG antibodies (FIGS. 5C & D) where inhibited by melibiose and Galα(1,3)Gal and Gal pep 1 but not glucose or CD48 pep 1 (SEQ ID No. 11). The concentration of peptide or sugar which inhibited the binding of antibody or lectin by 50% was calculated as a measurement of relative affinity (Table 1): 0.3 mM Gal pep 1 inhibited the binding of IB4 compared with 0.3 mM melibiose or <0.03 mM Galα(1,3)Gal 10 mM Gal pep 1 inhibited the binding of the anti-Galα(1,3)Gal IgG compared with 0.125 mM–0.3 mM melibiose and 0.03 mM Galα(1,3)Gal. Neither the CD48 pep 1 nor glucose had any effect on the binding of antibody or lectin.

EXAMPLE 2

RECOGNITION OF HUMAN MUCIN PEPTIDES BY ANTI-GALα(1,3)GAL ANTIBODIES

Materials and Methods

Cells

The pig EC cell line (PIEC) was obtained from Dr Ken Welsh (Churchill Hospital, Oxford, UK). MUC1+3T3 cells (MOR5 cells), produced by introducing cDNA encoding human MUC1 into murine 3T3 cells, were obtained from Dr Daniel Wreschner, (Tel Aviv University, Ramat Aviv, Israel).

Antibodies, Lectin and Saccharides.

Normal human serum (NHS) was obtained from 10 healthy volunteers, pooled and heat inactivated at 56° C. for 30 minutes before use. Purified human anti-Galα(1,3)Gal IgG antibodies were isolated from NHS by firstly fractionation of IgG on a Protein G Sepharose column (Pharmacia LKB Biotechnology, Sweden), followed by affinity chromatography on Galα(1,3)Galβ(1,4)GluNAc coated glass beads (Syntesome, N.J.). FITC conjugated sheep anti-human IgM, sheep anti-mouse IgG and horse radish peroxidase (HRP) conjugated sheep anti-human IgM or IgG were obtained from Silenus Laboratories Pty. Ltd., Australia. HRP conjugated streptavidin was obtained from Amersham International, UK. The BC2 mAb, which recognises the APDTR epitope of the human MUC1 molecule, is described elsewhere [23,24]. The IB4 lectin from *Griffonia simplififolia*, which binds to Galα(1,3)Gal [22], was obtained from Sigma, USA and was labelled with FITC or biotin [14,9]. Melibiose (Galα(1,6)Glc) and glucose (Sigma) were >99% pure. The Galα(1,3)Gal disaccharide, either free or coupled to BSA, was obtained from Dextra Laboratories, UK.

Peptide Synthesis

Peptides were synthesised using an Applied Biosystems Model 430A automated synthesiser (Applied Biosystems, USA) based on the standard Merrifield solid phase synthesis method [25]. All reagents for synthesis were purchased from Applied Biosystems. Crude peptides were purified by reversed phase high performance liquid phase chromatography (HPLC) (Waters Associates, USA) on a C-8-Aquapore RP-300 column using a gradient solvent system of 0.1% aqueous trifluoroacetic acid/actenonitrile. The purity of synthetic peptides was >90% as judged by HPLC analysis. Peptides were dissolved in phosphate buffered saline (PBS) prior to use in the serological assays. The peptides used in this study are listed in Table 2 (SEQ ID No. 1 and 11–26).

Serological Assays

Peptides or carbohydrates were examined cytofluorographically for their ability to inhibit antibody/lectin binding to the cell surface using a FACSCAN flow cytometer (Becton Dickinson, USA)[20]: 25 μl of inhibitor was mixed with 25 μl of antibody of lectin and incubated at 22° C. for 3 hours (peptides) or at 4° C. for 16 hours (carbohydrates) [14], prior to addition of appropriate targets. An Elisa assay was used to calculate the relative affinities of the sugars or the peptides for both IB4 lectin and antibodies, and were defined as the molar concentration of inhibitor giving 50% inhibition of the maximal binding of lectin or antibody.

Transfection Studies

COS cells transfection experiments were performed using DEAE Dextran [13] and a cDNA clone encoding human MUC1 [6], or a cDNA clone encoding the porcine α(1,3) galactosyltransferase [16]. As additional controls, COS cells were also transfected with the vector lacking an insert (mocj transfections). Indirect immunofluorescence was performed on cell monolayers in 6 well tissue culture plates using fluoresceinated IB4 lectin (which binds only to Galα(1,3) Gal), or anti-MUC1 monoclonal antibodies, 3E1.2[4] and VA1[28] and immunopurified sheep anti-mouse IgM or IgG to detect antibody binding.

Histological Analysis

Fresh or formalin fixed human tissue was incubated with biotinylated IB4 lectin (at 100 μg/ml) for 50 min at 22° C., washed, incubated with streptavidin-HRP for one hour, followed by diaminobenzidine (Amershal International, UK) at 1.5 mg/ml with 0.05% $H_2O_2$ for 5 min, prior to the removal of excess substrate by washing in running tap water for 3 min. The sections were counterstained with haematoxylin, mounted and examined microscopically. Tissues staining was graded independently by two investigators and scored as: 0 (no staining) to 4 (very strong staining).

Results

Our previous studies had shown that:
(a) natural human antibodies of the IgM and IgG classes bound to a single epitope in the pig, Galα(1,3)Gal (IB4 lectin binds the same epitope) [15,16,17];
(b) the antibodies and IB4 lectin could also bind to the synthetic peptide DAHWESWL (SEQ ID No. 1). During these studies and testing the specificity of peptide binding, it was apparent that the anti-Galα(1,3)Gal reagents (antibodies or IB4 lectin) could also bind to other peptides—notably those of the protein core of several mucins.

Figure 6A:
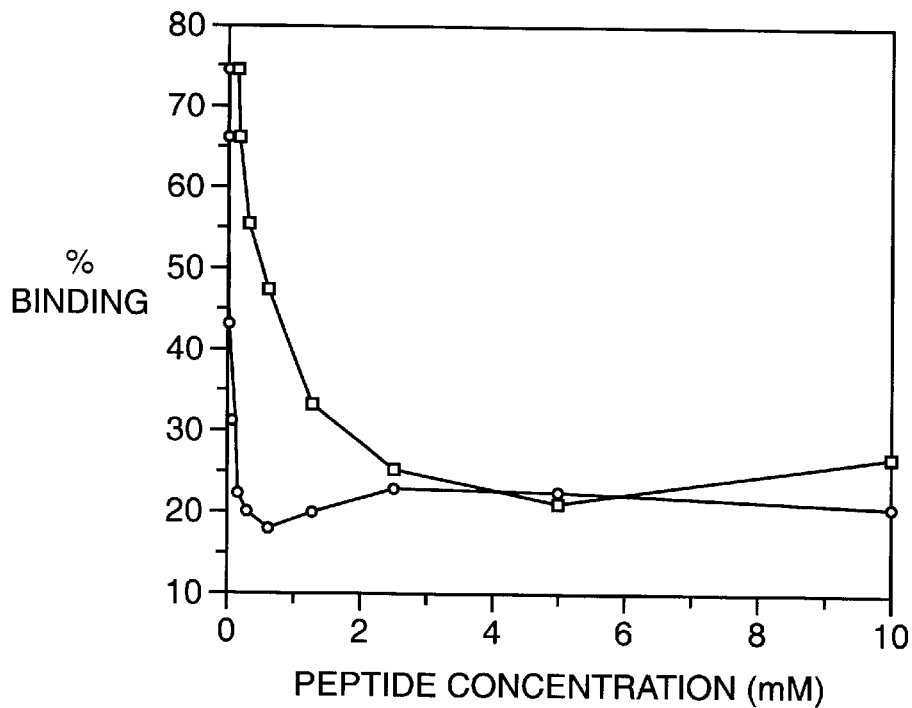
Figure 6B:
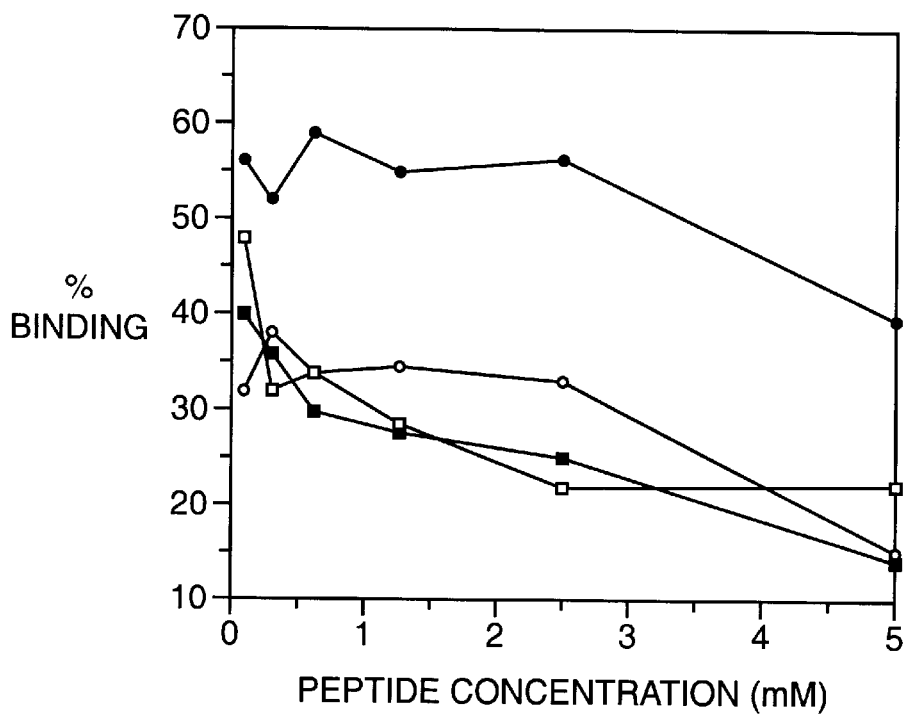

Blocking IB4 Binding to Galα(1,3)Gal Expressing Pig Cells by Mucin Deprived Peptides Muc pep 1, derived from the MUC1 VNTR, could block the binding of IB4 lectin to the cell surface of PIEC cells (FIG. 6); there was almost complete inhibition of binding to a concentration of 0.125 mM—indeed, the inhibition by the MUC1 VNTR peptide was greater than that found with the previously identified IB4 lectin binding peptide, Gal pep 1 (FIG. 6a). When other peptides derived from the VNTR region of MUC 1 were examined (see Table 2 for sequences), complete inhibition was observed with Muc pep2 and Muc pep 3, and partial inhibition with Muc pep 4 and Muc pep 5 (FIG. 6b). The data can be reformatted as % inhibition at 5 mM to show comparative binding (FIG. 7), with the same trend was noted at 2 other concentrations (data not shown). Muc pep6, derived from sequence amino terminal to the VNTR, showed partial inhibition; by contrast Muc pep 7, derived from the same region, did not (FIG. 7). Muc pep 8, derived from sequence carboxy terminal to the VNTR, also inhibited IB4 binding to PIEC cells (FIG. 7). Peptides derived from the VNTR regions of other human mucin molecules showed variable results: Muc pep 9, derived from the VNTR region of MUC 2, did not inhibit binding, whereas both Muc pep 10 and Muc pep 11, derived from the VNTR region of MUC3 and MUC4 respectively, inhibited IB4 binding (FIG. 7). Thus, peptides derived from the VNTR and elsewhere in MUC1 can inhibit the interaction of IB4 with its ligand, Galα(1,3)Gal. It should be noted that these peptides have been used to produce anti-mucin mAbs which specifically recognise the immunogenic peptide and there were no cross-reactions of the antibodies with other peptides, although the sequences are similar [23].

Inhibition of Binding of IB4 and Anti-Galα(1,3)Gal Antibodies to Galα(1,3)Gal by Mucin Peptides.

Figure 8A:
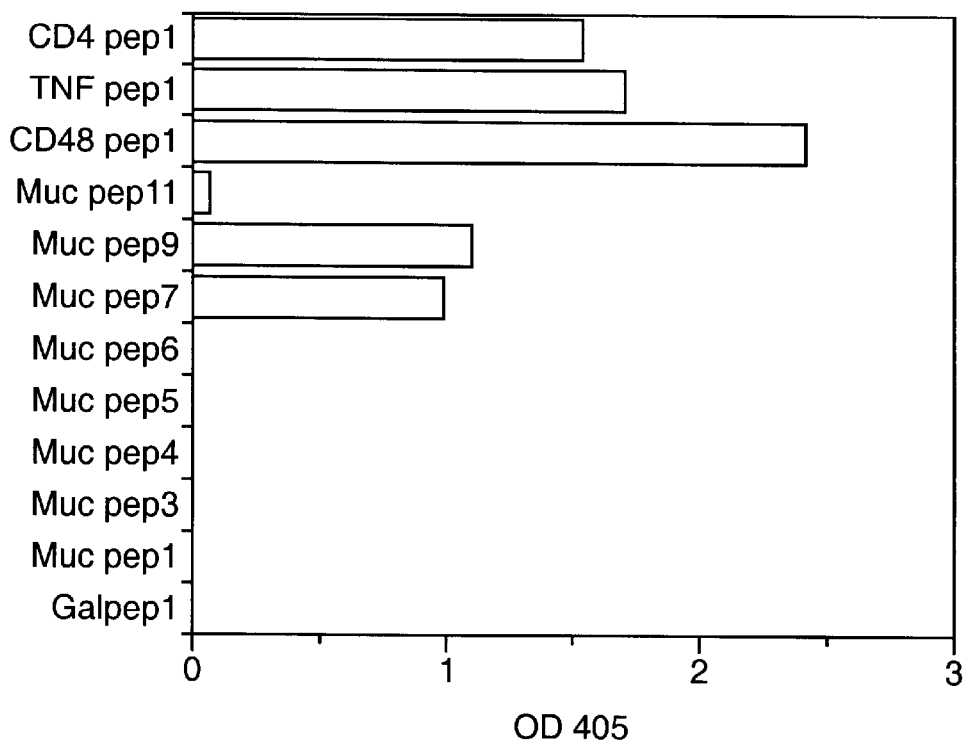

Mucin peptides were also examined for their ability to block the binding of IB4 lectin and anti-Galα(1,3)Gal IgG to the oligosaccharide epitope Galα(1,3)Gal-BSA bound in a microplate using an Elisa test (FIG. 8). At a peptide concentration of 5 mM, complete inhibition of binding of IB4 was observed with peptides Muc pep 1 (SEQ ID Nos. 15, 17–20 and 25, respectively), Muc pep 3 (SEQ ID Nos. 15, 17–20 and 25, respectively), Muc pep 4 (SEQ ID Nos. 15, 17–20 and 25, respectively), Muc pep 5 (SEQ ID Nos. 15, 17–20 and 25, respectively), Muc pep 6 (SEQ ID Nos. 15, 17–20 and 25, respectively) and Muc pep 11 (SEQ ID Nos. 15, 17–20 and 25, respectively) (FIG. 8a). By contrast Muc pep 7 (SEQ ID No. 21 and SEQ ID No. 23) and Muc pep 9 (SEQ ID No. 21 and SEQ ID No. 23) gave no inhibition of binding. Gal pep 1 (SEQ ID No. 1) inhibited as previously described, and the control peptides CD48 pep 1 (SEQ ID Nos. 11, 12 and 14, respectively), CD4 pep 1 (SEQ ID Nos. 11, 12 and 14, respectively) and TNF pep 1 (SEQ ID Nos. 11, 12 and 14, respectively) did not inhibit IB4 binding (FIG. 8a).

Figure 8B:
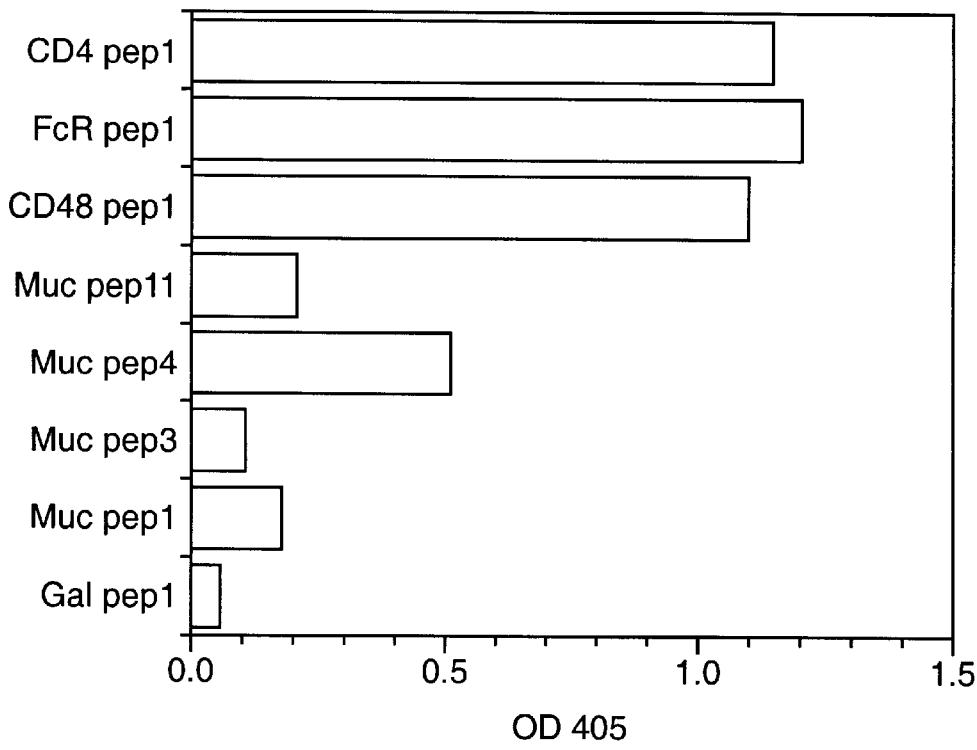

In accord with the inhibition results obtained previously with human antibodies, a higher concentration of Gal pep 1 was required to inhibit the binding of the purified human anti-Galα(1,3)Gal IgG antibody than with the IB4 lectin (FIG. 8b). The three peptides tested from the VNTR region of human MUC1:- Muc pep 1, Muc pep 3 and Muc pep 11 inhibited the binding of anti-Galα(1,3)Gal IgG (FIG. 8b), with Muc pep 4 showing partial inhibition. The three control peptides (CD48 pep 1, CD pep 1 and FcR pep 1) had no effect (FIG. 8b).

Relative Affinities of Mucin Peptides for Galα(1,3)Gal.

Elisa results were used to calculate the relative affinity of the mucin peptides for the IB4 lectin and for human anti-Galα(1,3)Gal antibodies, and to compare these with the affinity for α-galactosyl sugars. Biotinylated IB4 lectin and purified anti-Galα(1,3)Gal IgG antibodies were titered and for the affinity experiments were used at two dilutions less than that required to give 50% of the maximum $OD_{405}$ reading; the concentration of peptide or sugar which inhibited the binding of antibody or lectin by 50% was calculated as a measurement of relative affinity (Table 3). The studies showed that 0.3 mM Gal pep 1 (SEQ ID No. 1) inhibited the binding of IB4 compared with <0.03 mM Galα(1,3)Gal; 0.078 mM Muc pep 1 (SEQ ID No. 16), 0.625 mM Muc pep 3 (SEQ ID No. 17), 0.975 mM Muc pep 4 (SEQ ID No. 18), w.5 mM Muc pep 5 (SEQ ID No. 19), 1.25 mM Muc pep 6 (SEQ ID No. 20) and 0.156 mM Muc pep 11 (SEQ ID No. 25) inhibited the binding of IB4, 0.03 mM Galα(1,3)Gal inhibited the binding of the anti-Galα(1,3)Gal IgG compared with 2.5 mM pep 1, 3.75 mM Muc pep 3 (SEQ ID No. 17), 5 mM Muc pep 4 (SEQ ID No. 18) and 2.5 mM Muc pep 11 (SEQ ID No. 25) (Table 3). All the mucin peptides inhibited at a lower concentration that Gal pep 1 (SEQ ID No. 1) (10 mM). Neither the CD48 pep 1 (SEQ ID Nos. 11, 26), Scram pep 1 (a random peptide of Gal pep 1 sequence) (SEQ ID Nos. 11, 26), nor glucose had any effect on the binding of antibody or lectin.

Blocking of the Binding of Anti-mucin 1 mAb to Mucin 1 by Gal pep 1.

To extend these observations, the ability of Gal pep 1 (SEQ ID No. 1) to inhibit anti-MUC1 mAb, BC1, was examined. The BC1 mAb has been previously shown to specifically recognise the APDTR sequence of MUC1 VNTR [23]. The binding of BC1 to MUC1+3T3 cells was inhibited by Gal pep 1 down to a concentration of 0.156 mM (FIG. 9), in a similar fashion to Muc pep 1 (SEQ ID No. 15). These results show that, despite the lack of amino acid sequence similarity, the Muc pep 1 and Gal pep 1 peptides are equally recognised by the mAb, suggesting recognition of a secondary or tertiary structure.

Binding of IB4 to COS Cells Expressing MUC1 on the Cell Surface

We have previously shown that COS cells, derived from Old World monkeys, do not react with the IB4 lectin (ie. they do not express Galα(1,3)Gal), and that the Galα(1,3)Gal epitope can be expressed on the surface of these cells only after transfection with the porcine or mouse α(1,3) galactosyltransferase cDNA clones [16,17]. To examine whether expression of human MUC1 leads to IB4 binding, transfection of COS cells with the full length human MUC1 cDNA clone was performed. MUC1 could be detected on the COS cell surface by binding of the anti-MUC1 mAbs (FIG. 10 a&b), these cells were also reactive with the IB4 lectin (FIG. 19c). Thus native MUC1 polypeptide encodes amino acid sequences to which IB4 can bind. When COS cells transfected with the porcine α(1,3)galactosyltransferase cDNA clone were examined from anti-MUC1 mAb binding, weak staining was observed (data not shown).

Histological Analysis of IB4 Reactivity of Human Tissue

As IB4 and anti-Galα(1,3)Gal antibodies bind to mucin peptides, histological studies with biotinylated IB4 lectin on human normal or malignant tissues were performed. Using formalin fixed tissue, one of the normal breast tissues were reactive with the IB4 lectin, compared with 3 of 13 breast cancers which were reactive; 5 formalix fixed colon cancer samples did not bind IB4-biotin. The results with fresh tissue samples showed stronger binding of the IB4 lectin—0/3 normal breast tissue samples tested bound IB4 lectin, whereas 4/4 the breast cancer tissue were positive. With colon cancer tissues 3/7 were reactive, compared to 1/6 of the normal tissues. Representative samples of the histological analysis of human malignant tissues are shown (FIG. 11). Formalin fixed normal breast tissue which was not reactive with IB4-biotin, (FIG. 11a) infiltrating ductal breast carcinoma tissue (FIGS. 11b,c), where cytoplasmic staining with IB4-biotin is clearly shown (FIG. 11b) and cell surface staining of the lumen and glandular cells (FIG. 11c). Binding of the IB4 lectin was also demonstrated on fresh frozen human malignant tissue. Poorly differentiated, infiltrating ductal breast carcinoma tissue shows strong cytoplasmic staining with IB4-biotin (FIG. 11d), whereas staining of secretions in the lumen of glandular cells can be seen in a sample of moderately differentiated, infiltrating ductal breast carcinoma tissue (FIG. 11e). There is also strong staining of secretions and the cytoplasm of frozen sample of colon tissue (FIG. 11f).

Similar results to those obtained with the IB4 lectin were also found with purified human anti-Galα(1,3)Gal antibodies (FIG. 17A). Strong cytoplasmic and cell surface staining was noted in most samples—in those with luminal secretion these were also positive (FIG. 17A). It is important+to note that the staining was almost completely eliminated by absorbing the human serum with Galα(1,3)Gal beads so it no longer contained anti-Galα(1,3)Gal antibodies (FIG. 17B). Both of these studies clearly indicate that the staining of breast cancer was due to anti-Galα((1,3)Gal antibodies.

EXAMPLE 3

GAL PEP 1 AND MUC1 RESPONSE AND ANTI-TUMOUR ACTIVITY IN MOUSE MUC1+ TUMOURS

BALB/c or DBA/2 (H2$^d$) mice were immunised with the DAHWESWL peptide (Gal pep 1) (SEQ ID No. 1) coupled to KLH or with MUC1 fusion protein conjugated to oxidised mannan; 3 injections intraperitoneally (IP) were given weekly. It is important to note that mannan-MUC1 produces exceedingly good CTL based immune responses with protection from challenge with large numbers (50×10$^6$) of the tumour cells. The oxidised mannan-MUC1 gives high affinity CTLs, and little antibody, which are typical T$_1$ responses and such responses were confirmed herein (FIG. 12A). We noted that the DAHWESWL-KLH immunised mice challenged with MUC1+ tumour had similar degrees of protection, which was entirely specific for MUC1+P815 cells—there was no irnmunisation effect against P815 alone or other tumours (FIGS. 12B&14) i.e. the anti-tumour immunity appears to be directed to the MUC1+ cells.

The inventors previously showed that, in mice immunised with MUC1 peptide (not linked to mannan) had some protection evidenced by smaller tumours which disappeared earlier than in the controls. In the mannan-MUC1 immunised mice there was little or no tumour growth apparent at all, i.e. the mice are entirely protected by this mode of immunisation. Similarly, mice immunised with DAHWESWL-KLH had little or no tumour growth, i.e. the mice appeared to be immunised to the same extent with the DAHWESWL peptide as (SEQ ID No. 1) with the mannan-MUC1 peptide. The effect was clearly specific as DAHWESWL immunised mice had normal growth of P815 cells (FIG. 13). Two other MUC1+ tumour cell lines (MUC1+ 3T3 or MUC1+ P815) were used in protection experiments and a similar degree of protection was noted (not shown).

It was next determined whether the mice carrying established MUC1+ tumours could be immunised with the DAHWESWL peptide (SEQ ID No. 1). It was clearly noted that a rapid reversal of tumour growth occurred (not shown) and this was specific for MUC1.

The nature of the immune response to DAHWESWL (SEQ ID No. 1) was further examined. The studies were performed in the knowledge that MUC1 peptides induce Class I restricted CTL responses—the MUC1 epitopes have been mapped and although do not contain typical K$^d$, D$^d$ or L$^d$ binding motifs they satisfactorily bind H-2 class I molecules with high affinity. The DBA/2 mice immunised with DAHWESWL peptide produced anti-DAHWESWL and anti-MUC1 antibodies and CTLs. In addition, anti-MUC1 CTLs were also produced and appeared to have the same or greater activity than those produced by MUC1 mannan conjugates (FIG. 14(A)) Clearly, DAHWESWL peptide could associate with Class I H2 molecules.

To determine which anti-MUC1 epitopes were reacting with the anti-DAHWESWL CTLs, epitope mapping studies were performed using 9-mer peptides each primer peptide differing from the preceding by one amino acid so that the whole 20 amino acid VNTR sequence could be scanned. The results were clear (FIG. 15), only the peptides containing the sequence SAPDTRPAP (SEQ ID No. 9) or APDTRPAPG (SEQ ID No. 10) could lead to target cell lysis. There was no lysis of target cells with the other 18 peptides from the VNTR (FIG. 15) providing an appropriate specificity control. Thus, DAHWESWL immunised mice could induce CTLs which react with precisely the same SAPDTRPAP/ APDTRPAPG sequences (SEQ ID No. 9/SEQ ID No. 10) which we have previously shown to bind to H-2D$^d$ and H-2L$^d$ class I molecules respectively. In addition, the same sequences can be recognised in H-2K$^b$ mice after immunisation with DAHWESWVL.

However, these sequences cannot be recognised on HLA-A2 molecules, where, to recognise MUC1-HLA-A2 complexes requires immunisation with DLHWASWV (SEQ ID No. 8) or a related sequence derived from the provided consensus sequence.

Molecular modelling studies were performed to determine whether the MUC1 and DAHWESWL (SEQ ID No. 1) sequences were capable of conforming to the same shape. The modelling studies were done with the knowledge obtained from the crystallisation with H-2D$^d$ and H-2L$^d$. By computer modelling, H-2D$^d$ and H-2L$^d$ molecules were modelled with DAHWESWL/SAPDTRPAP (SEQ ID No. 1/SEQ ID No. 9) and DAHWESWL/APDTRPAPG (SEQ ID No. 1/SEQ ID No. 10) respectively and it was clear that the DAHWESWL/SAPDTRPAP/APDTRPAPG peptides (SEQ ID No. 1/SEQ ID No. 9/SEQ ID No. 10) are capable of assuming the same shape—although at this point crystallisation with class I molecules containing the peptides will be required to confirm this. It should be noted that DAHWESWL and (S)APDTRPAP(G) peptides have a completely different amino acid sequence, thus shape is important.

It was next investigated whether the DAHWESWL peptide (SEQ ID No. 1) be presented by HLA-A2 could immunise for HLA-H2 presented MUC1 peptides. The inventors had previously found that (S)APDTRPAP(G) peptide sequence can also be presented by HLA-A2 (in addition to H-2D$^d$ and H-2L$^d$ as described above). However, HLA-A2/K$^b$ mice immunised with DAHWESWL-KLH could not generate CTLs which reacted with MUC1 HLA binding peptides when in the HLA-A2 class I groove (FIG. 16), although mouse autologous PHA blast targets were positive (restricting element here is K$^b$). This was not surprising and clearly demonstrates that the shape of the DAHWESWL, peptide (SEQ ID No. 1) in the H-2$^d$ groove is determined both by the peptide sequence and also by the class I sequence. Thus the DAHWESWL peptide (SEQ ID No. 1) gives highly specific immune responses which appear to be directed to the human MUC1 peptide presented by MUC class I molecules. However, we now show that DLH-WASWV (SEQ ID No. 8) induces CTL's in HLA-A2 mice which specifically lyse human breast cancer cell lines (FIG. 14(B)). DLHWASWV will therefore protect mice/humans against MUC1 positive tumours suggesting that the "W" molecules which are exposed and "stick out" are import ant in the recognition of the sequence by T-cells.

Thus using the examples provided for the Class I molecules $H-2D^d$, $H-2L^d$, $H-2K^b$ and HLA-A2 we can, by using the known peptide sequence, the known consensus sequences, and computer modeling, come up with mimicking peptide sequences which can immunize against MUC1 peptides presented by Class I molecules. Based on these examples, peptides binding to other Class I molecules of humans can be deduced.

It is to be recognised that the present invention has been described by way of example only and that modifications and/or alterations thereto which would be obvious to a person skilled in the art on the basis of the teaching herein are considered to be within the scope and spirit of the present invention as defined in the appended claims.

TABLE 1

Relative affinities of peptides and carbohydrates for IB4 and pure anti-Galα(1,3)Gal IgG.

| Inhibitor | $I_{50}^a$ (mM) | |
| --- | --- | --- |
|  | IB4[b] | anti-Galα(1,3)Gal IgG[c] |
| Carbohydrate: | | |
| Galα(1,3)Gal | <0.03 | 0.03 |
| Melibiose | 0.3 | 0.3–0.125 |
| Glucose | >20 | >20 |
| Peptide: | | |
| Gal pep 1 | 0.3 | 10 |
| CD48 pep 1 | >20 | >20 |

[a]$I_{50}$ is the concentration of peptide or sugar required to give 50% inhibition of antibody or lectin binding.
[b]Biotinylated IB4 lectin used at a final concentration of 6.25 μg/ml.
[c]Anti-Galα(1,3)Gal IgG used at a final concentration of 87 μg/ml.

TABLE 3

Relative affinity of peptides and sugars for IB4 lectin and pure anti-Galα(1,3)Gal IgG.

| Inhibitor | $I_{50}^a$ (mM) | |
| --- | --- | --- |
|  | IB4[b] | Anti-Galα(1,3)Gal[c] |
| Galα(1,3)Gal | <0.03 | 0.03 |
| Glucose | >20 | >20 |
| Gal pep 1 | 0.3 | 10 |
| CD48 pep1 | >20 | >20 |
| Muc pep1 | 0.078 | 2.5 |
| Muc pep3 | 0.625 | 3.75 |
| Muc pep4 | 0.975 | 5 |
| Muc pep5 | 2.5 | ND[d] |
| Muc pep6 | 1.25 | ND |
| Muc pep11 | 0.156 | 2.5 |
| Scram pep1 | >20 | >20 |

[a]$I_{50}$ is the concentration of peptide or sugar required to give 50% inhibition of antibody or lectin binding.
[b]Biotinylated IB4 lectin used at a final concentration of 6.25 μgs/ml.
[c]Anti-Galα(1,3)Gal antibody (IgG) at a final concentration of 87 μgs/ml.
[d]ND = not determined

REFERENCES

1. Apostolopoulos V. Xing P-X. Trapani J A. McKenzie I F C. (1993) *Br. J. Cancer* 67:713–720.
2. Arklie J. Taylor-Papadimitriou J. Bodmer W F. Eyan M. Millis R. (1981) *Int. J. Cancer*, 28:23–29
3. Burcell J. Gendler S. Taylor-Papadimitriou J. Girling A., Lewis A. Millis R. Lampost D. (1987) *Cancer Res.* 47:5476–7482
4. Gendler J D. Spicer A P. (1995) *Annu Rev Physiol* 265:607–634.
5. Hayes C E. Goldstein I J. (1974) *J Biol Chem* 249:1904–1914
6. Jerome K R. Bu D. Finn O J. (1992) *Cancer Res* 52:5985–5990
7. Joziasse D H. Shaper J H. Jabs E W. Shaper N C. (1991) *J Biol Chem* 266:6991–6698.
8. Larsen R D. Rivera-Marrero C A. Ernst L K. Cunmmings R D. Lowe J B.(1990) *J Biol Chem* 265:7055–7061
9. McKenzie I F C, Xing P-X, Vaughan H A, Prenzoska J. Dabrowski P L, Sandrin M S *Distribution of the major xenoantigen* (Galα(1,3)Gal) *for pig to human xenografts. Transplant Immunol* 1994; 2:81.

TABLE 2

Sequence of peptides used in this study (SEQ ID Nos. 1 and 11–26)

| Pepitide | Sequence | Description | Residues | Reference |
| --- | --- | --- | --- | --- |
| Gal pep1 (Seq ID No.1) | DAHWESWL | | | |
| CD48 PEP1 (Seq ID No.11) | YTFDQKIVEWDSRKSKC | human CD48 | | |
| CD4 pep1 (Seq ID No.12) | TECKHKGKVVSGKVLSY | murine CD4 | 133–149 | |
| FcR pep1 (Seq ID No.13) | RYHHYSSNFSIPKANHSHSGDYYCKGSL | MURINE FCRII$_{β2}$ | 144–157 | |
| TNF pep1 (Seq ID No.14) | LSGVRFSAARTAHPLPQKH | MURINE TNFβ | | |
| Muc pep1 (Seq ID No.15) | CPAHGVTSAPDTRPAPGSTAP | human Muc1 VNTR | 13–32 | |
| Muc pep2 (Seq ID No.16) | PAHGVTSAPDTRPAPGSTAP | human Muc1 VNTR | 13–32 | |
| Muc pep3 (Seq ID No.17) | PDTRAPGSTAPPAHGVTSAPDTR | human Muc1 VNTR | 1–24 | |
| Muc pep4 (Seq ID No.18) | APDTRPAPGSTAPPAH | human Muc1 VNTR | A-1-15 | |
| Muc pep5 (Seq ID No.19) | PAPGSTAPPAHGVTSA | human Muc1 VNTR | 5–20 | |
| Muc pep6 (Seq ID No.20) | TGSGHASSTPGGEKETSAQRSSVP | human Muc1 NH2 to VNTR | 31–35 | |
| Muc pep7 (Seq ID No.21) | RSSVPSSTEKNAVSMTSSVL | human Muc1 NH2 to VNTR | 51–70 | |
| Muc pep8 (Seq ID No.22) | TGFNQYKTEAASRVNL | human Muc1 COOH to VNTR | 408–423 | |
| Muc pep9 (Seq ID No.23) | KYPTTTPISTTTMVTPTPTPTGTQTPTTT | human Muc2 VNTR | | |
| Muc pep10 (Seq ID No.24) | CHSTPSFTSSITTTETTS | human Muc3 VNTR | | |
| Muc pep11 (Seq ID No.25) | TSSASTGHATPLPVTP | human Muc4 VNTR | | |
| Scram pep1 (Seq ID No.26) | WEADLHWS | scrambled Gal pep1 | | |

10. Merrifield R B. (1963) *J Am Chem Soc* 85:2149–2154
11. Merrifield R B: *Automated synthesis of peptides. Science* 1965; 150:178.
12. Oldenburg K R, Loganathan D, Goldstein I J, Schultz P G, Gallop M A: *Peptide ligands for a sugar-binding protein isolated from a random peptide library. Proc Natl A cad Sci USA* 1992; 89:5393.
13. Sandrin M S. Gumley T P. Henning M M. Vaughan H A. Gonez L J. Trapani J A. McKenzie I F C (1992) *J Immunol* 149:1636–1641
14. Sandrin M S. Vaughan H A. Dabrowski P L, McKenzie I F C: *Anti-pig IgM antibodies in human serum react predominantly with Gal(α1–3)Gal epitopes. Proc Natl Acad Sci USA* 1993;90:11391.
15. Sandrin M S Vaughan H A. McKenzie I F C. (1994) *Transplant Revs* 8:134–149.
16. Sandrin M S. Dabkowski P L. Henning M M. Mouhtouris E. McKenzie I F C. (1994) *Xenotransplantation* 1:81–88.
17. Sandrin M S. Vaughan H A. Dabrowski P L. McKenzie I F C. (1993) *Proc Natl Acad Sci USA* 90:11391–11395.
18. Sandrin M S. McKenzie I F C. (1994) *Immunol Revs* 141:169–190.
19. Stacker S A, Thompson C. Riglar C. McKenzie I F C. (1985) *J. Natl. Cancer Inst.* 75:801–811.
20. Vaughan H A, Henning M M, Purcell D F J, McKenzie I F C, Sandrin M S: *The isolation of cDNA clones for CD-48. Immunogenetics* 1991; 33:113
21. Vaughan H A, Loveland B E, Sandrin M S: Gal(α1–3) Gal is the major xenoepitope expressed on pig endothelial cells recognised by naturally occuring cytotoxic human antibodies. Transplantation 1994; 58:879.
22. Vaughan H A, McKenzie I F C, Sandrin M S: *Biochemical studies of pig xenoantigens detected by naturally occurring antibodies and the galactoseα1–3galactose reactive lextin.* Transplantation 1995; 59:102.
23. Xing P-X. Prenzoska. J. McKenzie I F C. (1992) *Mol Immunol* 29:641–650.
24. Xing P-X. Tjandra J J Stacker S A. Teh J G. Thompson C H. McLaughlin P J. McKenzie I F C. (1989) *Immunol Cell. Biol.* 67:813–185.
25. A. Singer et al., *J. Nat. Cancer Inst.* 86, 330 (1994)
26. J. Taylor-Papadimitriou and A. A. Epenetos, *Tib. Tech.* 12, 227 (1994)
27. X. P. Xing, J. Prenzoska, K. Quelch and I. F. C. McKenzie, *Cancer Res.* 52, 2310(1992)
28. D. L. Bamd, M. S. Lan, R. S. Metzgar and O. J. Finn, *Proc. Natl Acad Sci. U.S.A.* 86, 7159 (1989)
29. K. R. Jerome et al., *J. Immunol.* 151, 1654 (1993)
30. G. G. Ioannides et al., *J. Immunol.* 151, 3693 (1993)
31. V. Apostolopoulos, G. A. Pietersz and I. F. C. McKenzie, *Vaccine*, 14, 930 (1996)
32. V. Apostolopoulos, G. A. Pietersz, B. E. Loveland, M. S. Sandrin and I. F. C. McKenzie, *Proc. Natl. Acad. Sci. U.S.A.* 92, 10128 (1995) *Cytotoxic T lymphocyte precursor cell* (CTLp) *frequency determinations*: described in I. Lefkovits and H. Waldmann, *Immunology Today* 5, 265 (1984); C. Taswell, *J. Immunol.* 126, 1614 (1981); S. Fazekas D E S T. Groth. *J. Immunol. Methods* 49, R11 (1982)

What is claimed is:

1. A cancer vaccine for administration to a host comprising a peptide that binds to IB4 lectin and anti-Galα(1,3)Gal antibodies, and one or more pharmaceutically acceptable carrier or diluent, optionally in association with an appropriate carrier peptide or other therapeutic agent; wherein said peptide includes one or more of the following sequences:
   DAHWESWL (SEQ ID No. 1);
   DGHWANWV (SEQ ID No. 2);
   DGNWAIYV (SEQ ID No. 3);
   DADWAGFI (SEQ ID No. 4);
   DGHWDSWL (SEQ ID No. 5);
   VSTFDSWL (SEQ ID No. 6);
   GTSFDDWL (SEQ ID No. 7); and
   DLHWASWV (SEQ ID No. 8).

2. A method of treatment of a human patient suffering from, or prone to suffer from cancer, which comprises administering to said patient an effective amount of a cancer vaccine comprising a peptide that binds IB4 lectin and anti-Galα(1,3)Gal antibodies, and optionally one or more pharmaceutically acceptable carrier or diluent, optionally also in association with one or more appropriate carrier peptides or another therapeutic agent; wherein said peptide includes one or more of the following sequences:
   DAHWESWL (SEQ ID No. 1);
   DGHWANWV (SEQ ID No. 2);
   DGNWAIYV (SEQ ID No. 3);
   DADWAGFI (SEQ ID No. 4);
   DGHWDSWL (SEQ ID No. 5);
   VSTFDSWL (SEQ ID No. 6);
   GTSFDDWL (SEQ ID No. 7); and
   DLHWASWV (SEQ ID No. 8).

3. The method as claimed in claim 2 wherein said cancer is an adenocarcinoma.

4. A cancer vaccine comprising;
   a non-self peptide that binds i) in a groove of class 1 MHC molecules, ii) the IB4 lectin and iii) anti Galα-(1,3)Gal antibodies, with the proviso that two or more tandem repeat sequences of MUC1 are not contained within said non-self peptide.

5. The vaccine as claimed in claim 4 wherein said peptide comprises from between 5 and about 200 amino acids and includes the consensus sequence, ArXXArZ wherein:
   Ar is the same or different and is selected from tryptophan (W), phenylalanine (F) or tyrosine (Y);
   X is the same or different and is a small aliphatic or polar amino acid;
   Z is a branched aliphatic amino acid.

6. The vaccine as claimed in claim 5 wherein the peptide is DAHWESWL (SEQ ID No. 1).

7. The vaccine as claimed in claim 5 wherein the peptide is DLHWASWV (SEQ ID No. 8).

8. The vaccine, as claimed in claim 4, wherein said peptide binds in a groove of class 1 MHC molecules in the same way as MUC1.

9. A method for the treatment or prophylaxis of cancer comprising;
   1) providing: i) a vaccine comprising a non-self peptide that binds a) in a groove of class 1 MHC molecules, b)

the IB4 lectin, and c) anti Galα-(1,3)Gal antibodies, with the proviso that two or more tandem repeat sequences of MUC1 are not contained within said non-self peptide and ii) a patient; and 2) administering said vaccine to said patient.

10. The method as claimed in claim 9 wherein said peptide comprises from 5 to about 200 amino acids and includes the consensus sequence, ArXXArZ wherein:

Ar is the same or different and is selected from tryptophan (W), phenylalanine (F) or tyrosine (Y);

X is the same or different and is a small aliphatic or polar amino acid;

Z is a branched aliphatic amino acid.

11. The method as claimed in any one of claim 10 wherein said peptide includes one or more of the following sequences:

DAHWESWL (SEQ ID No. 1)

DGHWANWV (SEQ ID No. 2)

DGNWAIYV (SEQ ID No. 3)

DADWAGFI (SEQ ID No. 4)

DGHWDSWL (SEQ ID No. 5)

VSTFDSWL (SEQ ID No. 6)

GTSFDDWL (SEQ ID No. 7).

12. The method as claimed in claim 10 wherein the peptide is DAHWESWL (SEQ ID No. 1).

13. The method as claimed in claim 10 wherein the peptide is DLHWASWV (SEQ ID No. 8).

* * * * *

```
                         SEQUENCE LISTING

<160> NUMBER OF SEQ ID NOS: 26

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 1

Asp Ala His Trp Glu Ser Trp Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 2

Asp Gly His Trp Ala Asn Trp Val
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: single
      stranded linear peptide
```

```
<400> SEQUENCE: 3

Asp Gly Asn Trp Ala Ile Tyr Val
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 4

Asp Ala Asp Trp Ala Gly Phe Ile
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 5

Asp Gly His Trp Asp Ser Trp Leu
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 6

Val Ser Thr Phe Asp Ser Trp Leu
 1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 7

Gly Thr Ser Phe Asp Asp Trp Leu
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 8

Asp Leu His Trp Ala Ser Trp Val
 1               5

<210> SEQ ID NO 9
<211> LENGTH: 9
<212> TYPE: PRT
```

```
<213> ORGANISM: Artificial Sequence
<220> FEATURE:
<223> OTHER INFORMATION: Description of Artificial Sequence: single
      stranded linear peptide

<400> SEQUENCE: 9

Ser Ala Pro Asp Thr Arg Pro Ala Pro
 1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 10

Ala Pro Asp Thr Arg Pro Ala Pro Gly
 1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 11

Tyr Thr Phe Asp Gln Lys Ile Val Glu Trp Asp Ser Arg Lys Ser Lys
 1               5                  10                  15

Cys

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 12

Thr Glu Cys Lys His Lys Lys Gly Lys Val Val Ser Gly Lys Val Leu
 1               5                  10                  15

Ser Tyr

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 13

Arg Tyr His His Tyr Ser Ser Asn Phe Ser Ile Pro Lys Ala Asn His
 1               5                  10                  15

Ser His Ser Gly Asp Tyr Tyr Cys Lys Gly Ser Leu
                20                  25

<210> SEQ ID NO 14
<211> LENGTH: 19
<212> TYPE: PRT
<213> ORGANISM: Artificial Sequence
<220> FEATURE:
```

```
<223> OTHER INFORMATION: Description of Artificial Sequence: single
      stranded linear peptide

<400> SEQUENCE: 14

Leu Ser Gly Val Arg Phe Ser Ala Ala Arg Thr Ala His Pro Leu Pro
 1               5                  10                  15

Gln Lys His

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 15

Cys Pro Ala His Gly Val Thr Ser Ala Pro Asp Thr Arg Pro Ala Pro
 1               5                  10                  15

Gly Ser Thr Ala Pro
            20

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 16

Pro Ala His Gly Val Thr Ser Ala Pro Asp Thr Arg Pro Ala Pro Gly
 1               5                  10                  15

Ser Thr Ala Pro
            20

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 17

Pro Asp Thr Arg Ala Pro Gly Ser Thr Ala Pro Pro Ala Ala Gly Val
 1               5                  10                  15

Thr Ser Ala Pro Asp Thr Arg
            20

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 18

Ala Pro Asp Thr Arg Pro Ala Pro Gly Ser Thr Ala Pro Pro Ala His
 1               5                  10                  15

<210> SEQ ID NO 19
<211> LENGTH: 16
<212> TYPE: PRT
```

```
<213> ORGANISM: Artificial Sequence
<220> FEATURE:
<223> OTHER INFORMATION: Description of Artificial Sequence: single
      stranded linear peptide

<400> SEQUENCE: 19

Pro Ala Pro Gly Ser Thr Ala Pro Pro Ala His Gly Val Thr Ser Ala
  1               5                  10                  15

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 20

Thr Gly Ser Gly His Ala Ser Ser Thr Pro Gly Gly Glu Lys Glu Thr
  1               5                  10                  15

Ser Ala Gln Arg Ser Ser Val Pro
             20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 21

Arg Ser Ser Val Pro Ser Ser Thr Glu Lys Asn Ala Val Ser Met Thr
  1               5                  10                  15

Ser Ser Val Leu
             20

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 22

Thr Gly Phe Asn Gln Tyr Lys Thr Glu Ala Ala Ser Arg Val Asn Leu
  1               5                  10                  15

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 23

Lys Tyr Pro Thr Thr Thr Pro Ile Ser Thr Thr Thr Met Val Thr Pro
  1               5                  10                  15

Thr Pro Thr Pro Thr Gly Thr Gln Thr Pro Thr Thr Thr
             20                  25

<210> SEQ ID NO 24
<211> LENGTH: 18
<212> TYPE: PRT
```

```
<213> ORGANISM: Artificial Sequence
<220> FEATURE:
<223> OTHER INFORMATION: Description of Artificial Sequence: single
      stranded linear peptide

<400> SEQUENCE: 24

Cys His Ser Thr Pro Ser Phe Thr Ser Ser Ile Thr Thr Thr Glu Thr
  1               5                  10                  15

Thr Ser

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 25

Thr Ser Ser Ala Ser Thr Gly His Ala Thr Pro Leu Pro Val Thr Pro
  1               5                  10                  15

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: single
      stranded linear peptide

<400> SEQUENCE: 26

Trp Glu Ala Asp Leu His Trp Ser
  1               5
```